United States Patent
Lindsey et al.

(10) Patent No.: US 6,924,375 B2
(45) Date of Patent: Aug. 2, 2005

(54) FACILE SYNTHESIS OF 1,9-DIACYLDIPYRROMETHANES

(75) Inventors: Jonathan S. Lindsey, Raleigh, NC (US); Shun-Ichi Tamaru, Fukuoka (JP); Lianhe Yu, High Point, NC (US)

(73) Assignee: North Carolina State University, Raleigh, NC (US)

( * ) Notice: Subject to any disclaimer, the term of this patent is extended or adjusted under 35 U.S.C. 154(b) by 149 days.

(21) Appl. No.: 10/654,181

(22) Filed: Sep. 3, 2003

(65) Prior Publication Data

US 2005/0054858 A1 Mar. 10, 2005

(51) Int. Cl.$^7$ .......................... C07F 7/00; C07D 487/22

(52) U.S. Cl. .................. 548/108; 540/145; 556/87; 556/407

(58) Field of Search .................. 548/108; 540/145; 556/87, 407

(56) References Cited

PUBLICATIONS

Lee et al., Tetrahedron, vol. 51, No. 43, pp. 11645–11672 (1995).*

* cited by examiner

Primary Examiner—Porfirio Nazario-Gonzalez
(74) Attorney, Agent, or Firm—Myers Bigel Sibley & Sajovec, PA

(57) ABSTRACT

The present invention provides a method of making a metal complex. The method comprises the steps of: (a) acylating a dipyrromethane or a 1-monoacyldipyrromethane to form a mixed reaction product comprising a 1,9-diacyldipyrromethane; (b) combining the reaction product with a compound of the formula $R_2MX_2$ in the presence of a base, where R is alkyl or aryl, M is Sn, Si, Ge, or Pb (preferably Sn), and X is halo, OAc, acac, or OTf, to form a product comprising a metal complex of the formula $DMR_2$ in the mixed reaction product, wherein D is a 1,9-diacyldipyrromethane; and then (c) separating the metal complex from the mixed reaction product. The method may be utilized for the convenient synthesis and separation of 1,9-diacyldipyrromethanes. Metal complex intermediates useful in such methods are also described.

23 Claims, 1 Drawing Sheet

FACILE SYNTHESIS OF 1,9-DIACYLDIPYRROMETHANES

This invention was made with Government support under Grant No. GM36238 from the National Institutes of Health. The Government has certain rights to this invention.

FIELD OF THE INVENTION

This invention concerns methods and intermediates useful for the synthesis of 1,9-diacyldipyrromethanes, along with methods of use thereof.

BACKGROUND OF THE INVENTION

Diacyldipyrromethanes are critical intermediates in porphyrin synthesis. P. Rao et al., *J. Org. Chem.* 2000, 65, 7323–7344. The reduction of a 1,9-diacyldipyrromethane affords the corresponding diol, which upon reaction with a dipyrromethane affords the meso-substituted porphyrin. With a diacyldipyrromethane bearing A, B, and C substituents at the 1, 5, and 9 positions, respectively, and a dipyrromethane bearing a D substituent at the respective 5-position, porphyrins bearing up to four different meso-substituents are readily prepared (ABCD-porphyrins). The availability of diacylation procedures that are efficient, mild, and scalable is essential for the smooth preparation of diverse porphyrins.

The methods for acylation of a dipyrromethane depend on whether the substituents at the 1- and 9-positions are the same or different. With identical substituents, the dipyrromethane (1) can be treated with excess EtMgBr, generating the dipyrromethane analog of the "pyrrole Grignard reagent," followed by excess acid chloride. The reaction typically yields a mixture of the intermediate 1-monoacyldipyrromethane (2) and the desired 1,9-diacyldipyrromethane (3) (Scheme 1). Diacyldipyrromethanes rarely crystallize well. Accordingly, the mixture is usually separated by chromatography, which can be tedious owing to the tending of the acyl-dipyrromethanes to streak on chromatographic media.

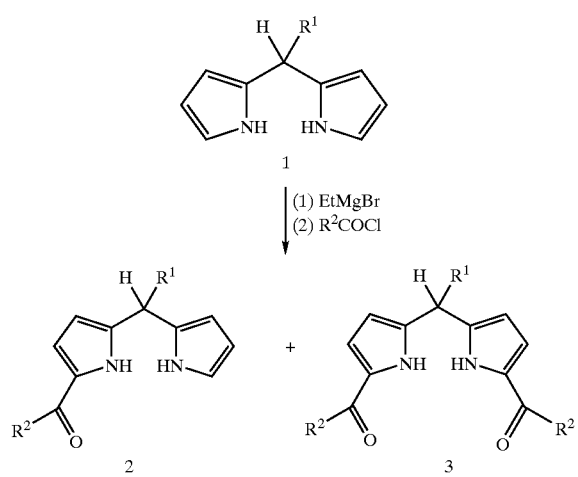

Scheme 1

Other methods of diacylation different from those of Scheme 1 are also available.

With different substituents at the 1- and 9-positions, a stepwise synthesis is required. The first step entails reaction of the dipyrromethane with EtMgBr followed by a 2-S-pyridyl benzothioate, which exclusively and efficiently gives the monoacyldipyrromethane (2). P. Rao et al., *J. Org. Chem.* 2000, 65, 1084–1092. Reaction of the latter with EtMgBr followed by an acid chloride is employed to obtain the 1,9-diacyldipyrromethane (3). P. Rao et al., *J. Org. Chem.* 2000, 65, 7323–7344. Again, the diacyldipyrromethane is purified by chromatography. If acylated sequentially, the 1- and 9-substitutents ($R^2$) can be different.

There remains a need for improvements in the synthesis of diacyldipyrromethanes, particularly for the introduction of two identical substituents. Indeed, the limitations of the one-step diacylation procedure are such that the two-step procedure is often employed instead. The acylation of a dipyrromethane at both α-positions would seem to be a straightforward matter, given the various methods available for the facile acylation of pyrrole. H. Anderson, et al., In *Pyrroles. Part I*, Jones, R. A.; Ed., John Wiley & Sons, Inc.: New York, 1990, pp 397–497. However, the diacylation of the dipyrromethane must be done under conditions that do not cause acidolysis of the linkage joining the two dipyrromethanes.

SUMMARY OF THE INVENTION

Here we describe new approaches for the facile preparation of 1,9-diacyldipyrromethanes. Our work was motivated by the dual objectives of achieving a more simple method of isolating the diacyldipyrromethane, and broadening the scope of accessible substituents. Our work was inspired by progress in two unrelated areas: (1) The recent work on use of diverse, mild Lewis acids in Friedel-Crafts acylations of arenes. C. Le Roux, Dubac, *J. Synlett* 2002, 181–200; S. Kobayashi, et al., *Chem. Rev.* 2002, 102, 2227–2302; A. Kawada, et al., *Bull. Chem. Soc. Jpn.* 2000, 73, 2325–2333. (2) The report that a 1,9-dicarbomethoxydipyrromethane formed a stable N,N-dibutyltin complex. C. Kitamura, et al., *J. Chem. Soc., Perkin Trans.* 1 1997, 1443–1447. Thus, we have examined acid-catalyzed acylations in lieu of Grignard reagents and have employed tin complexation as a means of isolating the 1,9-diacyldipyrromethane. Taken together, this work facilitates the preparation and isolation of 1,9-diacyldipyrromethanes without laborious chromatography.

In one embodiment, the present invention provides a method of making a metal complex, comprising: reacting a 1,9-diacyldipyrromethane with a compound of the formula $R_2MX_2$ in the presence of a base, where R is alkyl or aryl, M is Sn, Si, Ge or Pb (preferably Sn), and X is halo, OAc (where OAc is acetate), acac (acetylacetonate) or OTf (where OTf is triflate), to form a metal complex of the general formula $DMR_2$, wherein D is the 1,9-diacylodipyrromethane. Suitable bases include but are not limited to triethylamine, tributylamine, N,N-diisopropylamine, 1,8-diazabicyclo[5.4.0]undec-7-ene (or "DBU"), 1,5-diazabicyclo[4.3.0]non-5-ene (or "DBN"), and 2,6,-di-tert-butylpyridine.

Another aspect of the present invention is a metal complex of the general formula $DMR_2$, wherein D is a 1,9-diacyldipyrromethane, M is Sn, Si, Ge, or Pb (preferably Sn), and R is alkyl or aryl. In some embodiments the dipyrromethane may be substituted at the 5 position with a substituent selected from the group consisting of H, alkyl, and aryl; in other embodiments the dipyrromethane is substituted at the 5 position with a substituent selected from the group consisting of dipyrromethane, porphyrin, dipyrrin, and diacyldipyrromethane.

Metal complexes as described above are easily separated from the reaction mixture. The separated metal complex can then be used as an intermediate for the production of a variety of useful compounds, such as 1,9-diacyldipyrromethanes, which are in turn useful for the production of compounds such as porphyrin ring compounds, which are in turn useful for the production of solar cells, light harvesting arrays, and molecular memory devices.

The present invention is explained in greater detail in the drawings herein and the specification set forth below.

DETAILED DESCRIPTION OF THE PREFERRED EMBODIMENTS

Figure 1:
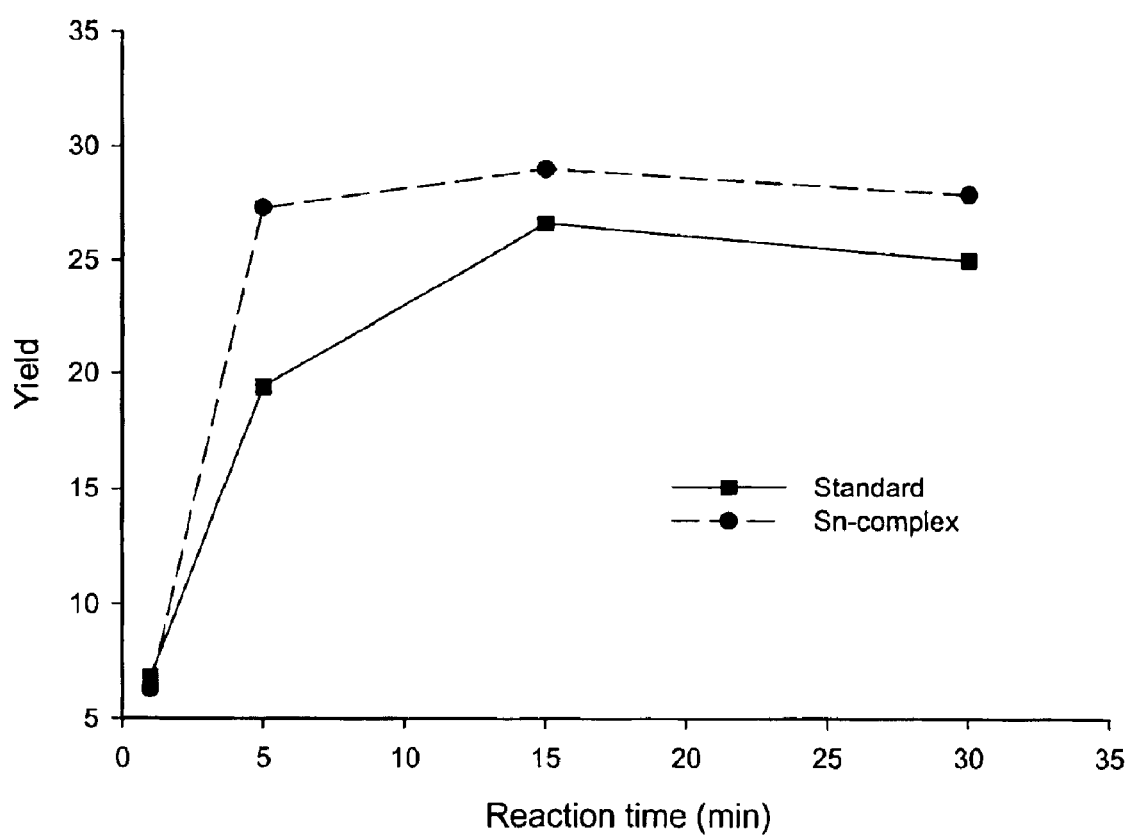
FIG. 1. The yield of porphyrin as a function of time upon reaction of dipyrromethane-dicarbinol 3 a-diol+ dipyrromethane 1a under catalysis by $Yb(OTf)_3$ in $CH_2Cl_2$ (the concentration of each reactant is 2.5 mM, the concentration of the catalyst is 3.2 mM). Each data point is the average from duplicate reactions.

"Alkyl," as used herein, refers to a straight or branched chain hydrocarbon containing from 1 to 10 or 20 carbon atoms, or more. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, and the like, which may be substituted or unsubstituted.

"Aryl," as used herein, refers to a monocyclic carbocyclic ring system or a bicyclic carbocyclic fused ring system having one or more aromatic rings. Representative examples of aryl include, azulenyl, indanyl, indenyl, naphthyl, phenyl, tetrahydronaphthyl, and the like, which may in turn be substituted or unsubstituted.

"Acyl" is intended to mean a —C(O)—R group, where R is a suitable substituent such as H, alkyl or aryl, which may in turn be substituted or unsubstituted.

"Dipyrromethane" as used herein includes unsubstituted or substituted dipyrromethane, which may be substituted one or more times at the 1, 2, 3, 5, 7, 8 or 9 positions with any suitable substituent such as halo, carbonyl, alkyl, fluoroalkyl including perfluoroalkyl, aryl (e.g., aryl at the 5 position; alkyl at the 1 and/or 9 position), fluoroaryl including perfluoroaryl, etc. Dipyrromethanes may be coupled to porphyrinic macrocycles at any suitable position on the dipyrromethanes, including the 1, 2, 3, 5, 7, 8, or 9 position.

"Halo" as used herein refers to chloro, fluoro, bromo, or iodo.

"Active Ester" as used herein refers to a compound which may be used to acylate a dipyrromethane or 1-acyldipyrromethane. In general an active ester is a compound of the general formula RCOX, where X is a leaving group. Any suitable leaving group may be used, including but not limited to alkylthio, arylthio, acyloxy (i.e., $(RCO)_2O$), 2,4-dinitrophenyloxy, etc.

"Vilsmeier reagent" as used herein refers to a composition comprised of a dialkylamide and $POCl_3$. The dialkylamide may be of the general formula RC(=O)NR'R', where R is H, alkyl or aryl, and R' is alkyl, an example of such a dialkylamide being N-acylmorpholide.

"Reducing agent" as used herein refers to a compound that donates electrons, which may be accompanied by protons.

"Solid support" as used herein may be any suitable solid support. Solid supports may take any physical form, such as gels, beads, particles, larger shaped articles, etc., and may be made of any suitable material such as an organic polymer or an inorganic material such as glass or silica.

As noted above, the present invention provides a method of making a metal complex, comprising the steps of: (a) acylating a dipyrromethane or a 1-monoacyldipyrromethane to form a mixed reaction product comprising a 1,9-diacyldipyrromethane; (b) combining the reaction product with a compound of the formula $R_2MX_2$ in the presence of a base, where R is alkyl or aryl, M is Sn, Si, Ge, or Pb (preferably Sn), and X is halo, OAc, acac, or OTf, to form a mixed reaction product comprising a metal complex of the formula $DMR_2$, wherein D is a 1,9-diacyldipyrromethane; and then (c) separating the metal complex from the mixed reaction product. Suitable bases include but are not limited to triethylamine, tributylamine, N,N-diisopropylamine, DBU, DBN, and 2,6-di-tert-butylpyridine. The time and temperature of the combining step is not critical, but may for example be from 1 or 2 minutes to 24 hours in duration, and is most conveniently carried out for 10 minutes to two hours, at a temperature range of $-20°$ C. to 50 or $100°$ C. or more (e.g., room temperature). Any suitable organic solvent may be used, including but not limited to methylene chloride, chloroform, 1,2-dichloroethane, toluene, chlorobenzene, etc.

Different starting materials may be used in the processes described herein. As will be appreciated, the acylating step (a) above may be carried out with a dipyrromethane as a starting material (that is, having H at the 1- and 9-positions), which is thereby acylated at the 1 and 9 position to produce said 1,9-diacyldipyrromethane. In the alternative, the acylating step (a) may be carried out with a 1-monoacyldipyrromethane as the starting material (that is, having an existing acyl group at the 1-position and H at the 9-position), which is thus acylated at the 9 position to produce the 1,9-diacyldipyrromethane. Depending upon the end use planned for the product, the dipyrromethane or 1-monoacyldipyrromethane starting material may be substituted at the 5 position with H, alkyl, or aryl; or in other embodiments may be substituted at the 5 position with a substituent such as a dipyrromethane, porphyrin, dipyrrin, or diacyldipyrromethane (which substituent may be directly coupled at the 5 position or coupled by an intermediate linking group such as an alkyl or aryl group).

Acylation of the starting material may be carried out in any of a variety of ways. In one embodiment, the acylating step (a) is carried out by reacting the dipyrromethane or 1-monoacyldipyrromethane with a compound of the formula $R^3COX$, where $R^3$ is alkyl or aryl and X is halo, to form a mixed reaction product comprising a 1,9-diacyldipyrromethane acylated at the 1 and 9 positions with $R^3CO$—. In another embodiment, the acylating step (a) is carried out by reacting the dipyrromethane or 1-monoacyldipyrromethane with an acid chloride and a Grignard reagent to form the mixed reaction product comprising a 1,9-diacyldipyrromethane. In another embodiment, the acylating step (a) is carried out by reacting the dipyrromethane or 1-monoacyldipyrromethane with an active ester to form the mixed reaction product comprising a 1,9-diacyldipyrromethane. In another embodiment, the acylating step (a) is carried out by reacting the dipyrromethane or 1-monoacyldipyrromethane with a Vilsmeier reagent to form the mixed reaction product comprising a 1,9-diacyldipyrromethane. See, e.g., D. Gryko et al., *J. Porphyrins Phthalocyanines* 7, 239–248 (2003).

Where complexation of the diacyldipyrromethane is carried out with a compound of the formula $R_2MX_2$, that compound may be free in the reaction solution or immobilized on a solid support such as a polymer support, where the groups R constitute a portion of the polymer or are otherwise coupled to the polymer (with immobilization on the solid support facilitating the subsequent separation of the acylated dipyrromethane product).

The methods described herein may further comprise the step of: (d) treating the metal complex with an acid to produce a 1,9-diacyldipyrromethane. Any suitable acid may be used, including but not limited to trifluoroacetic acid, trichloroacetic acid, acetic acid, HCl, p-toluenesulfonic acid.

In other embodiments, the methods described herein may further comprise the steps of: (d) reducing the metal complex with a base such as $NaBH_4$ to form a diol from the 1,9-diacyldipyrromethane; and then (e) condensing the diol with a dipyrromethane to form a porphyrin ring compound therefrom.

Utility. The separated metal complex can then be used as an intermediate for the production of a variety of useful compounds, such as 1,9-diacyldipyrromethanes, which are in turn useful for the production of compounds such as porphyrin ring compounds or porphyrinic macrocycles. The porphyrinic macrocycles are useful, among other things, for the production of polymers thereof which may be immobilized or coupled to a substrate and used as light harvesting rods, light harvesting arrays, and solar cells, as described for example in U.S. Pat. No. 6,407,330 to Lindsey et al. or U.S. Pat. No. 6,420,648 to Lindsey. Porphyrinic macrocycles are also useful immobilized to a substrate for making charge storage molecules and information storage devices containing the same. Such charge storage molecules and information storage devices are known and described in, for example, U.S. Pat. No. 6,208,553 to Gryko et al.; U.S. Pat. No. 6,381,169 to Bocian et al.; and U.S. Pat. No. 6,324,091 to Gryko et al. The porphyrinic macrocycle may comprise a member of a sandwich coordination compound in the information storage molecule, such as described in U.S. Pat. No. 6,212,093 to Li et al. or U.S. Pat. No. 6,451,942 to Li et al.

The present invention is explained in greater detail in the following non-limiting Examples.

EXAMPLES

Experimental Section

General. $^1$H NMR (400 MHz) and $^{13}$C NMR (100 MHz) were collected routinely in $CDCl_3$. Antimony(V) chloride, p-toluoyl chloride, and dibutyltin dichloride were obtained from Aldrich. $ClCH_2CH_2Cl$ (A.C.S. grade) was used as received.

Non-Commercial Compounds. The dipyrromethanes 1a, 1b, 1c, 1d, 1e, and 1f; the monoacyldipyrromethanes 2a and 2c; the diacyldipyrromethanes 3a, 3b, 3c, 3d, 3f, 3g, 3h, 3j, and 3k; bis(dipyrromethane) 7; and 3,5-di-tert-butylbenzoyl chloride were prepared following literature procedures. B. J. Littler, et al., *J. Org. Chem.* 1999, 64, 1391–1396; P. Rao et al., *J. Org. Chem.* 2000, 65, 7323–7344; G. R. Geier, III, et al., *J. Porphyrins Phthalocyanines* 2001, 5, 810–823; C. L. Honeybourne, et al., *Tetrahedron* 1980, 36, 1833–1838; C. K. Chang, *J. Org. Chem.* 1981, 46, 4610–4612; A. Wickramasinghe, et al., *Tetrahedron* 2001, 57, 4261–4269; C.-H. Lee, et al., *Tetrahedron* 1994, 50, 11427–11440; M. A. Korshunov, et al., *Zh. Org. Khim.* 1967, 3, 140–143. The known Mukaiyama reagents 6a 6b, 6c, 6d, and 6f were prepared using the refined procedure described below. P. Rao et al., *J. Org. Chem.* 2000, 65, 1084–1092; P. Rao et al., *J. Org. Chem.* 2000, 65, 7323–7344.

Tin Complexation of a Diacyldipyrromethane. Exemplified for Dibutyl[5,10-dihydro-1,9-bis(4-methylbenzoyl)-5-phenyldipyrrinato]tin(IV) [3a-Sn(Bu)$_2$]. A solution of 1,9-bis(4-methylbenzoyl)-5-phenyldipyrromethane (3a, 916 mg, 2.00 mmol, 500 mM) in $CH_2Cl_2$ (4.00 mL) was treated with TEA (814 μL, 6.00 mmol, 1.50 M) and $Bu_2SnCl_2$ (608 mg, 2.00 mmol, 500 mM) at room temperature. After 1 h, TLC analysis [silica, $CH_2Cl_2$/ethyl acetate (7:1), $R_f$ (3a)=0.5; $R_f$ (3a-Sn(Bu)$_2$)=1.0] indicated complete reaction. Removal of solvent and chromatography [silica (6×12 cm), $CH_2Cl_2$] afforded a pale green solid. The green solid was dissolved in diethyl ether (1 mL). Methanol (5 mL) was added, affording a precipitate. The precipitate was collected by filtration, and then dried in vacuo, affording a colorless solid (1.25 g, 90%): mp 155–157° C. (dec); $^1$H NMR δ 0.65–0.78 (m, 6H), 1.08–1.54 (m, 10H), 1.65–1.73(m, 2H), 2.45 (s, 6H), 5.61 (s, 1H), 6.20 (d, J=4.0 Hz, 2H), 7.10 (d, J=4.0 Hz, 2H), 7.18–7.35 (m, 9H), 7.84 (d, J=8.0 Hz, 4H); $^{13}$C NMR δ 13.65, 13.68, 21.6, 24.0, 24.8, 26.0, 26.3, 27.26, 27.33, 45.7, 115.2, 123.7, 126.7, 128.2, 128.7, 129.12, 129.18, 135.0, 135.8, 142.2, 144.3, 151.5, 184.5. Anal. Calcd for $C_{39}H_{42}N_2O_2Sn$: C, 67.94; H, 6.14; N, 4.06. Found: C, 67.83; H, 6.14; N, 4.05.

Dibutyl(5,10-dihydro-1,9-diformyl-5-phenyldipyrrinato)tin(IV) [3b-Sn(Bu)$_2$]. Following the general procedure described above, reaction of 3b (278 mg, 1.00 mmol) with TEA (418 μL, 3.00 mmol) and $Bu_2SnCl_2$ (304 mg, 1.00 mmol) for 50 min at room temperature afforded colorless solid after chromatography and precipitation (438 mg, 86%): mp 100–102° C.; $^1$H NMR δ 0.71–0.79 (m, 6H), 1.11–1.21 (m, 2H), 1.22–1.1.28 (m, 2H), 1.29–1.35 (m, 2H), 1.38–1.47 (m, 4H), 1.58–1.62 (m, 2H), 5.53 (s, 1H), 6.15 (d, J=4.0 Hz, 2H), 7.06 (d, J=4.0 Hz, 2H), 7.13–7.7.15 (m, 2H), 7.19–7.22 (m, 1H), 7.257.27 (m, 2H) 9.16 (s, 1H); $^{13}$C NMR δ 13.44, 13.48, 23.80, 24.36, 25.97, 26.25, 26.99, 27.03, 45.1, 115.4, 123.8, 126.8, 128.0, 128.6, 137.8, 143.5, 152.0, 178.5; FAB-MS obsd 511.1404, calcd 511.1408 [(M+H)$^+$]. Anal. Calcd for $C_{25}H_{30}N_2O_2Sn$: C, 58.97; H, 5.94; N, 5.50. Found: C, 58.97; H, 6.01; N, 5.51.

Dibutyl[5,10-dihydro-1,9-dimesitoyl-5-mesityldipyrrinato]tin(IV) [3c-Sn(Bu)$_2$]. Following the general procedure described above, reaction of 3c (278 mg, 0.500 mmol) with TEA (209 μL, 1.50 mmol) and $Bu_2SnCl_2$ (152 mg, 0.500 mmol) for 1 h at room temperature afforded a slightly pink solid after chromatography and precipitation (355 mg, 90%): mp 97–99° C.; $^1$H NMR δ 0.76–0.85 (m, 6H), 1.18–1.38 (m, 4H), 1.51–1.56 (m, 2H), 1.60–1.65 (m, 4H), 1.69 (s, 3H), 1.74–1.76 (m, 2H), 2.21 (s, 6H), 2.23 (s, 6H), 2.28 (s, 3H), 2.31 (s, 6H), 2.51 (s, 3H), 5.74 (d, J=3.9 Hz, 2H), 5.92 (s, 1H), 6.59 (d, J=3.9 Hz, 2H), 6.77 (s, 1H), 6.88–6.89 (m, 4H), 6.94 (s, 1H); $^{13}$C NMR δ 13.5, 19.48, 19.53, 20.12, 20.71, 20.87, 21.12, 23.82, 25.49, 26.46, 26.94, 27.61, 28.05, 39.8, 114.2, 123.6, 128.17, 128.19, 128.70, 130.7, 134.62, 134.84, 135.11, 135.77, 136.38, 136.50, 136.80, 137.95, 138.26, 152.4, 187.9; FAB-MS obsd 789.3442, calcd 789.3403 [(M+H)+]. Anal. Calcd for $C_{46}H_{56}I_2N_2O_2Sn$: C, 70.14; H, 7.17; N, 3.56. Found: C, 70.08; H, 7.29; N, 3.51.

Dibutyl(5,10-dihydro-1,9-diformyldipyrrinato)tin(IV) [3d-Sn(Bu)$_2$]. Following the general procedure described above, a suspension of 3d (202 mg, 1.00 mmol) in $CH_2Cl_2$ (10.0 mL) was treated with TEA (418 μL, 3.00 mmol) and $Bu_2SnCl_2$ (304 mg, 1.00 mmol) at room temperature for 40 min, resulting a clear solution. Chromatography and precipitation afforded a colorless solid (320 mg, 74%): mp 52–53° C.; $^1$H NMR δ 0.73 (t, J=7.2 Hz, 6H), 1.12–1.22 (m, 4H), 1.26–1.38 (m, 4H), 1.46–1.51 (m, 4H), 4.31 (s, 2H), 6.32 (d, J=3.6 Hz, 2H), 7.12 (d, J=3.6 Hz, 2H), 9.14 (s, 2H); $^{13}$C NMR δ 13.4, 23.8, 26.0, 27.0, 27.8, 114.1, 123.9, 137.8, 148.1, 178.0; FAB-MS obsd 435.1095, calcd 435.1083

[(M+H)$^+$]. Anal. Calcd for C$_{19}$H$_{26}$N$_2$O$_2$Sn: C, 52.69; H, 6.05; N, 6.47. Found: C, 52.98; H, 6.13; N, 6.23.

Dibutyl[5,10-dihydro-1,9-bis(4-methylbenzoyl) dipyrrinato]tin(IV) [3e-Sn(Bu)$_2$]. Following the general procedure described above, a suspension of 3e (191 mg, 0.500 mmol) in CH$_2$Cl$_2$ (5.0 mL) was treated with TEA (209 μL, 1.50 mmol) and Bu$_2$SnCl$_2$ (152 mg, 0.500 mmol) at room temperature for 40 min. Chromatography and precipitation afforded a colorless solid (263 mg, 85%): mp 118–120° C.; $^1$H NMR δ 0.66–0.71 (m, 6H), 1.10–1.17 (m, 4H), 1.31–1.40 (m, 4H), 1.53–1.58 (m, 4H), 2.44 (s, 6H), 4.34 (s, 2H), 6.33 (d, J=3.0 Hz, 2H), 7.13 (d, J=3.0 Hz, 2H), 7.30 (d, J=7.5 Hz, 4H), 7.82 (d, J=7.5 Hz, 4H); $^{13}$C NMR δ 13.5, 21.5, 24.1, 26.0, 27.2, 28.4, 113.8, 123.6, 129.02, 129.06, 135.03, 135.74, 142.0, 147.6, 183.9; FAB-MS obsd 615.2034, calcd 615.2067 [(M+H)$^+$]. Anal. Calcd for C$_{33}$H$_{38}$N$_2$O$_2$Sn: C, 64.62; H, 6.24; N, 4.57. Found: C, 64.88; H, 6.23; N, 4.63.

Dibutyl(5,10-dihydro-1,9-dihexanoyl-5-pentyldipyrrin ato)tin(IV) [3f-Sn(Bu)$_2$]. Following the general procedure described above, a solution of 3f (206 mg, 0.500 mmol) in CH$_2$Cl$_2$ (5.0 mL) was treated with TEA (209 μL, 1.50 mmol) and Bu$_2$SnCl$_2$ (152 mg, 0.500 mmol) at room temperature. After 1 h TLC analysis (silica, CH$_2$Cl$_2$) indicated incomplete consumption of the starting material. Therefore an additional amount of Bu$_2$SnCl$_2$ (30 mg, 0.10 mmol) was added and the reaction mixture was stirred for another 20 min. Chromatography (silica, CH$_2$Cl$_2$) afforded a slightly yellow oil (302 mg, 93%): $^1$H NMR δ 0.66–0.75 (m, 6H), 0.77–0.82 (m, 6H), 0.87–0.92 (m, 6H), 0.99–1.02 (m, 2H), 1.13–1.16 (m, 6H), 1.24–1.40 (m, 8H), 1.46–1.51 (m, 2H), 1.59–1.65 (m, 2H), 1.68–1.80 (m, 6H), 2.60–2.81 (m, 4H), 4.27 (t, J=6.3 Hz, 1H), 6.24 (d, J=3.6 Hz, 2H), 7.07 (d, J=3.6 Hz, 2H); $^{13}$C NMR δ 13.37, 13.51, 13.88, 13.96, 22.40, 22.46, 22.53, 25.04, 25.92, 16.25, 26.35, 26.45, 27.01, 27.28, 31.62, 31.70, 36.2, 39.2, 41.9, 112.8, 120.0, 136.4, 151.9, 191.2; Anal. Calcd for C$_{34}$H$_{56}$N$_2$O$_2$Sn: C, 63.46; H, 8.77; N, 4.35. Found: C, 63.57; H, 8.82; N, 4.41.

Dibutyl[5,10-dihydro-1,9-bis(4-methoxybenzoyl)-5-phenyldipyrrinato]tin(IV) [3g-Sn(Bu)$_2$]. Following the general procedure described above, reaction of 3g (245 mg, 0.500 mmol) with TEA (209 μL, 1.50 mmol) and Bu$_2$SnCl$_2$ (152 mg, 0.500 mmol) for 40 min at room temperature afforded a colorless solid after chromatography and precipitation (329 mg, 91%): mp 108–110° C.; $^1$H NMR δ 0.66–0.75 (m, 6H), 1.08–1.50 (m, 8H), 1.60–1.69 (m, 4H), 3.88 (s, 6H), 5.59 (s, 1H), 6.18–6.19 (m, 2H), 6.99 (d, J=8.4 Hz, 4H), 7.08–7.09 (m, 2H), 7.21–7.28 (m, 5H), 7.93 (d, J=8.4 Hz, 4H); $^{13}$C NMR δ 13.52, 13.54, 23.9, 24.8, 25.88, 26.20, 27.12, 27.19, 45.5, 55.2, 113.6, 114.9, 123.1, 126.5, 127.98, 128.46, 130.1, 131.0, 135.6, 144.3, 150.9, 162.4, 183.4; FAB-MS obsd 723.2245, calcd 723.2253 [(M+H)$^+$]. Anal. Calcd for C$_{39}$H$_{42}$N$_2$O$_4$Sn: C, 64.93; H, 5.87; N, 3.88. Found: C, 65.05; H, 5.80; N, 3.91.

Dibutyl[5,10-dihydro-1,9-bis(pentafluorobenzoyl)-5-pentafluorophenyldipyrrinato] tin(IV) [3h-Sn(Bu)$_2$]. Following the general procedure described above, reaction of 3h (140 mg, 0.214 mmol) with TEA (90 μL, 0.642 mmol) and Bu$_2$SnCl$_2$ (65 mg, 0.21 mmol) for 20 min at room temperature afforded a purple solid after chromatography and precipitation (173 mg, 87%): mp 130° C. (dec); $^1$H NMR δ 0.77–0.84 (m, 6H), 1.23–1.31 (m, 4H), 1.45–1.53 (m, 4H), 1.64–1.72 (m, 4H), 6.09 (s, 1H), 6.11 (d, J=4.0 Hz, 2H), 6.88 (d, J=4.0 Hz, 2H); $^{13}$C NMR δ 13.1, 24.20, 24.48, 25.87, 26.04, 26.50, 26.79, 33.6, 112.4 (t), 115.6, 124.8, 136.1–136.5 (m), 138.6 (m), 140.8 (m), 142.4 (m), 143.4 (m), 145.0 (m), 145.9 (m), 149.8, 172.4; FAB-MS obsd 933.0620, calcd 933.0648 [(M+H)$^+$]. Anal. Calcd for C$_{37}$H$_{23}$F$_{15}$N$_2$O$_2$Sn: C, 47.72; H, 2.49; N, 3.01. Found: C, 47.91; H, 2.43; N, 3.02.

Dibutyl[5,10-dihydro-1,9-bis(trifluoroacetyl)-5-phenyldipyrrinato]tin(IV) [3i-Sn(Bu)$_2$]. Following the general procedure described above, reaction of 3i (207 mg, 0.500 mmol) with TEA (209 μL, 1.50 mmol) and Bu$_2$SnCl$_2$ (152 mg, 0.500 mmol) for 40 min at room temperature afforded a brown oil after chromatography (137 mg, 42%): $^1$H NMR δ 0.71–0.81 (m, 6H), 1.11–1.22 (m, 2H), 1.24–1.33 (m, 4H), 1.35–1.45 (m, 2H), 1.49–1.55 (m, 2H), 1.65–1.71 (m, 2H), 5.58 (s, 1H), 6.27 (d, J=4.2 Hz, 2H), 7.11–7.14 (m, 2H), 7.27–7.36 (m, 5H); $^{13}$C NMR δ 13.31, 13.38, 24.05, 24.55, 25.77, 26.11, 26.88, 45.7, 118.2, 126.21, 126.25, 127.9, 129.0, 131.7, 141.8, 156.0, 169.169.6 (q); FAB-MS obsd 647.1155, calcd 647.1178 [(M+H)$^+$]. (C$_{27}$H$_{28}$F$_6$N$_2$O$_2$Sn). The compound decomposed slowly upon storage at room temperature, therefore, an elemental analysis was not performed.

Dibutyl[5,10-dihydro-1,9-bis(3-iodobenzoyl)-5-mesityldipyrrinato]tin(IV) [3j-Sn(Bu)$_2$]. Following the general procedure described above, reaction of 3j (362 mg, 0.500 mmol) with TEA (209 μL, 1.50 mmol) and Bu$_2$SnCl$_2$ (152 mg, 0.500 mmol) for 40 min at room temperature afforded a slightly yellow solid after chromatography and precipitation (426 mg, 89%): mp 124–126° C.; $^1$H NMR δ 0.71–0.82 (m, 6H), 1.16–1.36 (m, 6H), 1.46–1.55 (m, 4H), 1.72–1.76 (m, 2H), 2.32 (s, 6H), 2.51 (s, 3H), 5.84 (d, J=3.9 Hz, 2H), 5.92 (s, 1H), 6.81 (s, 1H), 6.99–7.02 (m, 3H), 7.21–7.23 (m, 2H), 7.84–7.89 (m, 4H), 8.20–8.21 (m, 2H); $^{13}$C NMR δ 13.6, 20.20, 20.69, 20.92, 23.52, 24.84, 26.15, 26.31, 27.42, 27.44, 39.9, 114.6, 124.5, 128.01, 128.74, 129.95, 130.71, 134.90, 135.84, 136.50, 137.50, 137.83, 139.54, 140.16, 152.8, 181.9; FAB-MS obsd 957.0436, calcd 957.0508 [(M+H)+]. Anal. Calcd for C$_{40}$H$_{42}$I$_2$N$_2$O$_2$Sn: C, 50.29; H, 4.43; N, 2.93. Found: C, 50.64; H, 4.45; N, 2.96.

Dibutyl[5,10-dihydro-1,9-bis(4-methylbenzoyl)-5-(4-trimethylsilylethynylphenyl) dipyrrinato]tin(IV) [3k-Sn(Bu)$_2$]. Following the general procedure described above, reaction of 3k (277 mg, 0.500 mmol) with TEA (209 μL, 1.50 mmol) and Bu$_2$SnCl$_2$ (152 mg, 0.500 mmol) for 40 min at room temperature afforded a colorless solid after chromatography and precipitation (374 mg, 95%): mp 74–76° C.; $^1$H NMR δ 0.22 (s, 9H), 0.68 (t, J=7.6 Hz, 3H), 0.73 (t, J=7.2 Hz, 3H), 1.09–1.25 (m, 4H), 1.28–1.44 (m, 4H), 1.48–1.53 (m, 2H), 1.62–1.66 (m, 2H), 5.56 (s, 1H), 6.12 (d, J=4.0 Hz, 2H), 7.07 (d, J=4.0 Hz, 2H), 7.15 (d, J=8.4 Hz, 2H), 7.29 (d, J=8.0 Hz, 4H), 7.38 (d, J=8.4 Hz, 2H), 7.82 (d, J=8.0 Hz, 4H); $^{13}$C NMR δ-0.07, 13.54, 13.58, 21.5, 24.05, 24.64, 25.92, 26.22, 27.19, 27.22, 45.5, 94.1, 104.9, 115.0, 121.5, 123.6, 128.1, 129.04, 129.09, 132.2, 134.8, 135.8, 142.2, 144.5, 150.7, 184.5; FAB-MS obsd 787.2758, calcd 787.2742 [(M+H)$^+$]. Anal. Calcd for C$_{44}$H$_{50}$N$_2$O$_2$SiSn: C, 67.26; H, 6.41; N, 3.57. Found: C, 67.37; H, 6.42; N, 3.55.

No Column Chromatography Purification for a Diacyldipyrromethane Sn-complex [3a-Sn(Bu)$_2$]. The diacylation of a dipyrromethane 1a (DPM; 1 g, [DPM]=200 mM, [SnCl$_4$]=400 mM, [p-toluoyl chloride]=250 mM in ClCH$_2$CH$_2$Cl) and subsequent Sn complexation ([diacyl DPM]=100 mM, [Bu$_2$SnCl$_2$]=100 mM, [TEA]=300 mM in CH$_2$Cl$_2$) were carried out following the general procedure (vide supra). The crude mixture from the tin complexation was dissolved in CH$_2$Cl$_2$ (100 mL) and silica (20 mL, an amount equal to 9 g) was added. The mixture was evaporated to dryness. Hexanes (100 mL) was added and the mixture was sonicated for 10 min. Then the mixture was filtered in a Büchner funnel (Whatmann type 40 filter paper). The filtered material was washed by hexanes (300 mL) and the eluent was combined with the initial filtrate. The combined filtrate and eluent was evaporated to afford the crude diacyldipyrromethane as a brown solid (1.32 g, coarse yield; 43%). The brown residue was dissolved in Et$_2$O, then MeOH was added causing formation of a precipitate. The precipitate was collected by filtration and the filtrate was reconcentrated. The precipitation method was repeated twice more. The precipitates were combined affording the target material as a pale yellow solid (1.10 g, yield; 38%) with satisfactory analytical data (mp, $^1$H NMR spectrum, and elemental analysis).

Grignard Method for Diacylation with Subsequent Tin Complexation. Exemplified for 3a-Sn(Bu)$_2$. A THF solution of 1 M EtMgBr (11.3 mL, 11.3 mmol) was added slowly to a tap-water-cooled flask containing a solution of 5-phenyldipyrromethane (1a, 500 mg, 2.25 mmol) in toluene (45 mL) under argon. An exothermic reaction with gas evolution ensued. The resulting brown solution was stirred for 30 min at room temperature. Then a solution of p-toluoyl chloride (743 µL, 5.60 mmol) in toluene (5.6 mL) was added over 10 min. The reaction was stirred for an additional 10 min. The reaction was quenched with saturated aqueous NH$_4$Cl (35 mL) and ethyl acetate (45 mL). The organic phase was washed successively with water, brine and then dried (MgSO$_4$). The solvent was removed under reduced pressure. The resulting residue was dissolved in CH$_2$Cl$_2$ (22.5 mL). TEA (940 µL, 6.75 mmol) and Bu$_2$SnCl$_2$ (684 mg, 2.25 mmol) were added and the mixture was stirred at room temperature for 30 min. The reaction mixture was evaporated. Flash column chromatography (silica, 6.0×7 cm, CH$_2$Cl$_2$) removed the black material and gave a green eluent (350 mL). The green eluent was evaporated to dryness. The residue was dissolved in Et$_2$O, then MeOH was added causing formation of a precipitate. The precipitate was collected by filtration. The filtrate was concentrated and precipitated. This process was repeated once more. The precipitates were combined affording the target material as a pale yellow solid (713 mg, 46%). Analytical data (mp and $^1$H NMR spectrum) are consistent with the data reported below. Anal. Calcd for C$_{39}$H$_{42}$N$_2$O$_2$Sn: C, 67.94; H, 6.14; N, 4.06. Found: C, 68.10; H, 6.07; N, 4.09.

SbCl$_5$-Catalyzed Diacylation with Subsequent Tin Complexation. Exemplified for 3a-Sn(Bu)$_2$. Samples of 5-phenyldipyrromethane (1a, 1.11 g, 5.00 mmol) and p-toluoyl chloride (1.32 mL, 10.0 mmol) were dissolved in ClCH$_2$CH$_2$Cl (100 mL). SbCl$_5$ (1.34 mL, 10.0 mmol) was added all-at-once via syringe and the mixture was stirred for 5 min at room temperature. To hydrolyze the remaining acid chloride, water (100 µL) was added and the reaction mixture was stirred for 1 min. The reaction mixture was poured into 50 mL of saturated aqueous NaHCO$_3$ in a 250 mL Erlenmeyer flask. The biphasic mixture was stirred vigorously for 10 min and placed into a separatory funnel. The organic layer was collected, dried (Na$_2$SO$_4$) and filtered (Whatman type 40) in a Büchner funnel. The filtrate was concentrated to dryness. The resulting residue was dissolved in CH$_2$Cl$_2$ (10 mL). TEA (2.10 mL, 15.0 mmol) and Bu$_2$SnCl$_2$ (1.52 g, 5.00 mmol) were added and the mixture was stirred for 10 min at room temperature. The reaction mixture was evaporated. The black residue was subjected to flash column chromatography (silica, 6.0×7 cm, CH$_2$Cl$_2$). The black material bound at the top of the column and a green eluent was collected. The green eluent was evaporated to dryness affording an oily solid. The residue was dissolved in Et$_2$O and slowly evaporated at room temperature for 2–3 days to afford pale yellow crystals (2.00 g, 58%): mp>155° C. (dec.); $^1$H NMR δ 0.68 (t, 3H), 0.73 (t, 3H), 1.06–1.53 (m, 10H), 1.64–1.71 (m, 2H), 2.44 (s, 6H), 5.59 (s, 1H), 6.18 (d, J=3.6 Hz, 2H), 7.08 (d, J=3.6 Hz, 2H), 7.16–7.32 (m, 9H), 7.82 (d, J=8.0 Hz, 4H); $^{13}$C NMR δ 13.8, 21.8, 24.2, 25.0, 26.2, 26.5, 27.4, 27.5, 45.9, 115.3, 123.9, 126.9, 128.4, 128.8, 129.3, 129.4, 135.2, 136.0, 142.4, 144.5, 151.7, 184.7; FAB-MS obsd 691.2374, calcd 691.2347 (C$_{39}$H$_{42}$N$_2$O$_2$Sn); Anal. Calcd for C$_{39}$H$_{42}$N$_2$O$_2$Sn: C, 67.94; H, 6.14; N, 4.06. Found: C, 68.00; H, 6.15; N, 4.07. Alternatively, the residue from evaporation of the eluent of flash column chromatography was dissolved in Et$_2$O, then MeOH was added causing formation of a precipitate. The precipitate was collected by filtration and the filtrate was reconcentrated. The precipitation method was repeated twice. The precipitates were combined affording the target material as a pale yellow solid.

Synthesis of a Mukaiyama Reagent. Exemplified for S-2-Pyridyl 4-methylbenzothioate (6a). A solution of 2-mercaptopyridine (11.1 g, 100 mmol) in THF (100 mL) was treated with p-toluoyl chloride (15.5 g, 100 mmol) at room temperature. The resulting slurry was stirred for 30 min. The precipitate was collected by filtration (Whatman type 40) and washed with hexanes (150 mL) in a Büchner funnel. The filtered material was added into a biphasic solution of saturated aqueous NaHCO$_3$ (100 mL) and diethyl ether (100 mL) in a 250 mL Erlenmeyer flask. The mixture was stirred until the foaming subsided. The organic layer was removed and the water layer was extracted with diethyl ether. The organic layers were combined, dried (Na$_2$SO$_4$), and filtered. The filtrate was concentrated to afford a pale yellow solid. The $^1$H NMR spectrum of the yellow solid did not show any noticeable impurities. The yellow solid was dissolved in diethyl ether, then hexanes was added causing formation of a precipitate. The precipitate was collected by filtration. The filtrate was concentrated and precipitated. The precipitation method was repeated once more. The precipitates were combined, affording a colorless solid (22.3 g, 96%): mp 61–62° C.; $^1$H NMR δ 2.43 (s, 3H), 7.26–7.35 (m, 3H), 7.70–7.81 (m, 2H), 7.89–7.95 (m, 2H), 8.64–8.70 (m, 1H); Anal. Calcd for C$_{13}$H$_{11}$NOS: C, 68.09; H,4.84; N, 6.11. Found: C, 68.04; H, 4.78; N, 6.29.

S-2-Pyridyl 4-methoxybenzothioate (6b). Following the general procedure described above, reaction of p-anisoyl chloride (4.70 g, 30.0 mmol) with 2-mercaptopyridine (3.33 g, 30.0 mmol) in THF (30 mL) for 30 min at room temperature afforded pale yellow solid after precipitation (6.70 g, 91%): mp 73° C.; $^1$H NMR δ 3.88 (s, 3H), 6.93–7.00 (m, 2H), 7.30–7.34 (m, 1H), 7.70–7.74 (m, 2H), 7.75–7.80 (m, 1H), 7.97–8.02 (m, 1H), 8.64–8.69 (m, 1H); Anal. Calcd for C$_{13}$H$_{11}$NO$_2$S: C, 63.65; H, 4.52; N, 5.71. Found: C, 63.78; H, 4.59; N, 5.66.

S-2-Pyridyl pentafluorobenzothioate (6c). Following the general procedure described above, reaction of pentafluorobenzoyl chloride (6.92 g, 30.0 mmol) with 2-mercaptopyridine (3.33 g, 30.0 mmol) in THF (30 mL) for 30 min at room temperature afforded pale yellow solid after precipitation (7.97 g, 87%): mp 51° C.; $^1$H NMR δ 7.37–7.42 (m, 1H), 7.75–7.79 (m, 1H), 7.81–7.87 (m, 1H), 8.67–8.71 (m, 1H); Anal. Calcd for C$_{12}$H$_4$NOS: C, 47.22; H, 1.32; N, 4.59. Found: C, 47.59; H, 1.29; N, 4.38.

S-2-Pyridyl 4-iodobenzothioate (6d). Following the general procedure described above, reaction of 4-iodobenzoyl chloride (8.01 g, 30.0 mmol) with 2-mercaptopyridine (3.33 g, 30.0 mmol) in THF (60 mL) for 30 min at room temperature afforded pale yellow solid after precipitation (9.61 g, 94%): mp 127° C.; $^1$H NMR δ 7.30–7.38 (m, 1H), 7.70–7.76 (m, 3H), 7.77–7.83 (m, 1H), 7.84–7.89 (m, 2H), 8.64–8.71 (m, 1H); Anal. Calcd for $C_{12}H_8INOS$: C, 42.25; H, 2.36; N, 4.11. Found: C, 42.27; H, 2.38; N, 4.05.

S-2-Pyridyl 4-bromobenzothioate (6f). Following the general procedure described above, reaction of 4-bromobenzoyl chloride (13.17 g, 60.0 mmol) with 2-mercaptopyridine (6.67 g, 60.0 mmol) in THF (120 mL) for 30 min at room temperature afforded pale yellow solid after precipitation (16.2 g, 92%): mp 134° C.; $^1$H NMR δ 7.30–7.39 (m, 1H), 7.62–7.68 (m, 2H), 7.70–7.79 (m, 1H), 7.77–7.84 (m, 1H), 7.86–7.92 (m, 2H), 8.64–8.72 (m, 1H); Anal. Calcd for $C_{12}H_8BrNOS$: C, 49.00; H, 2.74; N, 4.76. Found: C, 49.28; H, 2.70; N, 4.83.

Synthesis of a Monoacyldipyrromethane. Exemplified for 1-(4-Methylbenzoyl)-5-phenyldipyrromethane (2a). A solution of EtMgBr (50.0 mL, 50.0 mmol, 1.0 M in THF) was added via syringe to a stirred solution of 1a (4.44 g, 20.0 mmol) in THF (20 mL) under argon. The mixture was stirred for 10 min at room temperature and then cooled to −78° C. A solution of 6a (4.58 g, 20.0 mmol) in THF (20 mL) was added. The mixture was stirred for 10 min at −78° C. Then the cooling bath was removed, the mixture was stirred for 20 min, and then the reaction was quenched with saturated aqueous $NH_4Cl$ (150 mL). The mixture was diluted with THF (10 mL), washed with water (100 mL), and then dried ($Na_2SO_4$). Removal of solvents and chromatography [silica (6×24 cm), $CH_2Cl_2$ (2300 mL)] afforded a golden amorphous solid (5.82 g, 86%): mp 69–70° C.; $^1$H NMR δ 2.43 (s, 3H), 5.55 (s, 1H), 5.95–6.01 (m, 1H), 6.05–6.09 (m, 1H), 6.14–6.18 (m, 1H), 6.67–6.71 (m, 1H), 6.79–6.82 (m, 1H), 7.20–7.35 (m, 7H), 7.72–7.76 (m, 2H), 8.05–8.22 (brs, 1H), 9.50–9.68 (brs, 1H); Anal. Calcd for $C_{23}H_{20}N_2O$: C, 81.15; H, 5.92; N, 8.23. Found: C, 80.74; H, 5.74; N, 8.25.

1-(4-Methoxybenzoyl)-5-[4-methoxyphenyl]dipyrromethane (2b). Following the general procedure described for the preparation of 2a, a solution of 1b (5.05 g, 20.0 mmol) in THF (20 mL) was treated with EtMgBr (50.0 mL, 50.0 mmol, 1.0 M in THF) and 6b (4.91 g, 20.0 mmol). The reaction was quenched 40 min after removal of the cooling bath. Chromatography [silica, $CH_2Cl_2$/hexanes (3:1)] afforded a pale yellow solid (4.32 g, 56%): mp 113–114° C.; $^1$H NMR δ 3.77 (s, 3H), 3.87 (s, 3H), 5.50 (s, 1H), 5.97–5.99 (brs, 1H), 6.06–6.10 (brs, 1H), 6.13–6.17 (brs, 1H), 6.66–6.69 (brs, 1H), 6.76–6.83 (m, 3H), 6.94 (d, J=8.8 Hz, 2H), 7.10 (d, J=8.8 Hz, 1H), 7.82 (d, J=8.4 Hz, 2H), 8.15–8.45 (brs, 1H), 9.74–9.95 (brs, 1H); $^{13}$C NMR δ 43.5, 55.5, 55.7, 107.8, 108.6, 110.5, 113.8, 114.3, 118.0, 120.3, 129.6, 130.9, 131.2, 131.4, 131.7, 133.2, 141.8, 158.9, 162.9, 183.7; FAB-MS obsd 386.1633, calcd 386.1630 ($C_{24}H_{22}N_2O_3$); Anal. Calcd for $C_{24}H_{22}N_2O_3$: C, 74.59; H, 5.74; N, 7.25. N, 7.25. Found: C, 74.58; H, 5.78; N, 7.22.

1-(4-Iodobenzoyl)-5-[4-[2-(trimethylsilyl)ethynyl]phenyl]dipyrromethane (2d). Following the general procedure described for the preparation of 2a, a solution of 1d (6.37 g, 20.0 mmol) in THF (40 mL) was treated with EtMgBr (50.0 mL, 50.0 mmol, 1.0 M in THF) and 6d (6.82 g, 20.0 mmol). The reaction was quenched 20 min after removal of the cooling bath. Chromatography [silica, $CH_2Cl_2$/hexanes (3:1)] afforded a foam-like solid (8.42 g, 77%): mp 102–103° C.; $^1$H NMR δ 0.25 (s, 9H), 5.54 (s, 1H), 5.92–5.98 (m, 1H), 6.00–6.09 (m, 1H), 6.12–6.18 (m, 1H), 6.66–6.70 (m, 1H), 6.74–6.79 (m, 1H), 7.10 (d, J=8.0 Hz, 2H), 7.33–7.40 (m, 2H), 7.45–7.53 (m, 2H), 7.78–7.85 (m, 2H), 8.24 (brs, 1H), 9.91 (brs, 1H); $^{13}$C NMR δ 0.06, 43.86, 94.6, 99.3, 104.7, 108.1, 108.4, 111.3, 118.1, 121.8, 122.0, 128.1, 130.4, 130.50, 130.54, 132.2, 137.5, 137.6, 141.3, 142.5, 184.0; FAB-MS obsd 548.0779, calcd 548.0781 ($C_{27}H_{25}IN_2OSi$); Anal. Calcd for $C_{27}H_{25}IN_2OSi$: C, 59.12; H, 4.59; N, 5.11. Found: C, 59.58; H, 4.77; N, 5.05.

1-(4-Iodobenzoyl)dipyrromethane (2e). Following the general procedure described for 2a, a solution of 1e (2.92 g, 20.0 mmol) in THF (40 mL) was treated with EtMgBr (50.0 mL, 50.0 mmol, 1.0 M in THF) and 6d (6.82 g, 20.0 mmol). The reaction was quenched 40 min after removal of the cooling bath. Chromatography [silica, $CH_2Cl_2$/hexanes (3:1)] afforded a pale yellow solid (3.54 g, 47%): mp 160–161° C. (dec.); $^1$H NMR δ 4.02 (s, 2H), 6.00–6.20 (m, 3H), 6.56–6.58 (m, 1H), 6.70–6.90 (m, 1H), 7.56 (d, J=8.4 Hz, 1H), 7.83 (d, J=8.4 Hz, 1H), 8.90–9.10 (brs, 1H), 10.70–10.90 (brs, 1H); $^{13}$C NMR δ 27.0, 99.3, 106.9, 108.7, 110.7, 117.9, 122.9, 127.8, 130.3, 130.6, 137.9, 141.2, 184.3; FAB-MS obsd 376.20, calcd 376.19 ($C_{16}H_{13}IN_2O$); Anal. Calcd for $C_{16}H_{13}IN_2O$: C, 51.08; H, 3.48; N, 7.45. Found: C, 50.92; H, 3.56; N, 7.22.

1-(4-Methylbenzoyl)-5-pentafluorophenyldipyrromethane (2f). Following the general procedure described for the preparation of 2a, a solution of 1c (6.24 g, 20.0 mmol) in THF (20 mL) was treated with EtMgBr (50.0 mL, 50.0 mmol, 1.0 M in THF) and a solution of 6a (4.59 g, 20.0 mmol) in THF (20 mL). The reaction was quenched 20 min after removal of the cooling bath. The dark residue obtained was precipitated with ethyl acetate/hexanes. The precipitate was collected by filtration. The mother liquor was concentrated and precipitated again with ethyl acetate/hexanes. The precipitate was collected and combined with the previous batch to afford a colorless foam-like solid (6.79 g, 79%): mp 164–165° C.; $^1$H NMR δ 2.44 (s, 3H), 5.94 (s, 1H), 6.04–6.09 (m, 1H), 6.11–6.13 (m, 1H), 6.15–6.19 (m, 1H), 6.72–6.76 (m, 1H), 6.78–6.81 (m, 1H), 7.28 (d, J=8.0 Hz, 2H), 7.77 (d, J=8.0 Hz, 2H), 8.38 (brs, 1H), 9.83 (brs, 1H); $^{13}$C NMR δ 21.6, 33.3, 108.2, 108.7, 110.3, 114.7, 114.9 (m), 115.0, 118.6, 120.5, 126.7, 129.1, 129.3, 131.0, 135.2, 136.5 (m), 137.8, 139.1 (m), 141.8 (m), 142.9, 143.7 (m), 146.1 (m), 184.9; FAB-MS obsd 430.1115, calcd 430.1105 ($C_{23}H_{15}F_5N_2O$); Anal. Calcd for $C_{23}H_{15}F_5N_2O$: C, 64.19; H, 3.51; N, 6.51. Found: C, 64.29; H, 3.47; N, 6.52.

Synthesis of Diacyldipyrromethanes.

$SnCl_4$ Catalyzed Acylation of a Monoacyldipyrromethane. Exemplified for 1,9-bis(4-methylbenzoyl)-5-phenyldipyrromethane (3a). Samples of 2a (1.70 g, 5.00 mmol) and p-toluoyl chloride (0.990 mL, 7.50 mmol) were dissolved in $CH_2Cl_2$ (10 mL). $SnCl_4$ (1.17 mL, 10.0 mmol) was added all-at-once and the mixture was stirred at room temperature for 30 min. TLC analysis showed two major spots: $R_f$=0.5, desired diacyldipyrromethane; and $R_f$=0.3, isomeric diacyldipyrromethane. Then the reaction mixture was poured into 100 mL of saturated aqueous $NaHCO_3$. The biphasic mixture was stirred vigorously for 10 min and then filtered through a Buchner funnel using filter paper (Whatmann type 40). The filtrate was placed into a separatory funnel. The organic layer was collected, dried ($Na_2SO_4$) and concentrated. Chromatography [silica (6×12 cm, $CH_2Cl_2$/ethyl acetate (10:1)] afforded the desired diacyldipyrromethane (3a) as a pale yellow foam-like solid (1.34 g, 59%) and an isomeric diacyldipyrromethane (5) as a pale yellow solid (215 mg, 9.3%). Data for 3a: mp 112–113° C.; $^1$H NMR δ 2.39 (s, 6H), 5.68 (s, 1H), 5.92–5.96 (m, 2H), 6.50–6.54 (m, 2H), 7.19 (d, J=8.0 Hz, 4H), 7.30–7.44 (m, 5H), 7.56 (d, J=8.0 Hz, 2H), 11.62 (brs, 2H); Anal. Calcd for $C_{31}H_{26}N_2O_2$: C, 81.20; H, 5.72; N, 6.11. Found: C, 81.12; H, 5.73; N, 6.07. Data for 5: mp 102–103° C.; $^1$H NMR δ

2.39 (s, 3H), 2.40 (s, 3H), 5.58 (s, 1H), 6.04–6.10 (m, 1H), 6.47 (s, 1H), 6.72–6.78 (m, 1H), 7.00–7.03 (m, 1H), 7.12–7.24 (m, 9H), 7.58 (d, J=8.0 Hz, 2H), 7.63 (d, J=8.0 Hz, 2H), 10.03 (brs, 1H), 11.09 (brs, 1H); $^{13}$C NMR δ 21.55, 21.61, 43.9, 109.2, 111.2, 121.7, 124.4, 126.3, 127.3, 128.3, 128.7, 128.8, 129.0, 129.1, 129.2, 131.0, 133.7, 135.4, 137.2, 140.0, 141.75, 141.79, 142.6, 185.1, 190.8; FAB-MS obsd 458.1991, calcd 458.1994 ($C_{31}H_{26}N_2O_2$).

Method A. $SbCl_5$ Catalyzed Acylation of a Monoacyldipyrromethane with Subsequent Tin Complexation. Exemplified for 3a-Sn(Bu)$_2$. Samples of 2a (1.70 g, 5.00 mmol) and p-toluoyl chloride (0.990 mL, 7.50 mmol) were dissolved in $CH_2Cl_2$ (100 mL). $SbCl_5$ (1.28 mL, 10.0 mmol) was added all-at-once and the mixture was stirred at room temperature for 10 min. TLC analysis [silica $CH_2Cl_2$/ethyl acetate (7:1)] showed two major spots: $R_f$=0.5, desired diacyldipyrromethane; and $R_f$=0.3, an isomeric diacyldipyrromethane. Then the reaction mixture was poured into 100 mL of saturated aqueous $NaHCO_3$. The biphasic mixture was stirred vigorously for 10 min and then filtered through a Büchner funnel using filter paper (Whatmann type 40). The organic layer was collected, dried ($Na_2SO_4$) and concentrated to dryness. The resulting residue was dissolved in $CH_2Cl_2$ (10 mL). TEA (2.10 mL, 15.0 mmol) and $Bu_2SnCl_2$ (1.52 g, 5.00 mmol) were added and the mixture was stirred at room temperature for 15 min. TLC analysis [silica, $CH_2Cl_2$/ethyl acetate (7:1)] showed two major spots, $R_f$=1.0, 3a-Sn(Bu)$_2$; and $R_f$=0.3, isomeric diacyldipyrromethane. The reaction mixture was concentrated. The black residue was purified by flash column chromatography (silica, 6.0×12 cm, $CH_2Cl_2$). Fast eluting green fractions were collected. The green fractions were combined and concentrated to dryness. The residue was dissolved in $Et_2O$ (2 mL), then MeOH (10 mL) was added causing formation of a precipitate. The precipitate was collected by filtration, and dried in vacuo to afford a pale yellow solid (2.26 g, 66%) with satisfactory analytical data (mp, $^1$H NMR spectrum, and elemental analysis).

Method B. $SnCl_4$ Catalyzed Acylation (500 mM) of a Monoacyldipyrromethane with Subsequent Tin Complexation. Exemplified for 3a-Sn(Bu)$_2$. Samples of 2a (1.70 g, 5.00 mmol) and p-toluoyl chloride (0.990 mL, 7.50 mmol) were dissolved in $ClCH_2CH_2Cl$ (10 mL). $SnCl_4$ (1.17 mL, 10.0 mmol) was added all-at-once and the mixture was stirred at room temperature for 10 min. TLC analysis [silica $CH_2Cl_2$/ethyl acetate (7:1)] showed two major spots: $R_f$=0.5, desired diacyldipyrromethane; and $R_f$=0.3, an isomeric diacyldipyrromethane. Then the reaction mixture was poured into 100 mL of saturated aqueous $NaHCO_3$. The biphasic mixture was stirred vigorously for 10 min and then filtered through a Büchner funnel using filter paper (Whatmann type 40). The filtrate was placed into a separatory funnel. The organic layer was collected, dried ($Na_2SO_4$) and concentrated to dryness. The resulting residue was dissolved in $CH_2Cl_2$ (20 mL). TEA (2.10 mL, 15.0 mmol) and $Bu_2SnCl_2$ (1.52 g, 5.00 mmol) were added and the mixture was stirred at room temperature for 15 min. TLC analysis [silica, $CH_2Cl_2$/ethyl acetate (7:1)] showed two major spots, $R_f$=1.0, 3a-Sn(Bu)$_2$; and $R_f$=0.3, isomeric diacyldipyrromethane. The reaction mixture was concentrated. The black residue was purified by flash column chromatography (silica, 6.0×10 cm, $CH_2Cl_2$). Fast eluting green fractions were collected. The green fractions were combined and concentrated to dryness. The residue was dissolved in $Et_2O$ (2 mL), then MeOH (10 mL) was added causing formation of a precipitate. The precipitate was collected by filtration, and dried in vacuo to afford a pale yellow solid (2.1 g, 60%) with satisfactory analytical data (mp, $^1$H NMR spectrum, and elemental analysis).

Method C. Grignard Method for Acylation of Monoacyl Dipyrromethanes with Subsequent Tin Complexation, Exemplified for 1,9-bis(4-methylbenzoyl)-5-phenyldipyrromethane [3a-Sn(Bu)$_2$]. A solution of 2a (1.70 g, 5.00 mmol) in dry toluene (20 mL) at room temperature was treated slowly with EtMgBr (30.0 mL, 30.0 mmol, 1.0 M solution in THF) under argon. After stirring for 10 min, p-toluoyl chloride (2.00 mL, 15.0 mmol) was added. Stirring was continued for 30 min. Then saturated aqueous $NH_4Cl$ (100 mL) and ethyl acetate (100 mL) were added. The organic layer was separated, washed with saturated aqueous $NaHCO_3$, dried ($Na_2SO_4$), and concentrated. The resulting residue was dissolved in $CH_2Cl_2$ (10 mL). Triethylamine (2.10 mL, 15.0 mmol) and $Bu_2SnCl_2$ (1.52 g, 5.00 mmol) were added and the mixture was stirred at room temperature for 15 min. The reaction mixture was evaporated. Flash column chromatography ($SiO_2$, 6.0×12 cm, $CH_2Cl_2$) afforded a green residue. The residue was precipitated with diethyl ether/methanol to afford a pale yellow solid (1.93 g, 56%) with satisfactory analytical data (mp, $^1$H NMR spectrum, and elemental analysis).

Dibutyl[5,10-dihydro-1-(4-methoxybenzoyl)-9-(4-methylbenzoyl)-5-(4-methoxyphenyl)dipyrrinato]tin(IV) [3l-Sn(Bu)$_2$]. Following a general procedure described in Method B, a reaction of 2b (1.93 g, 5.00 mmol) in $CH_2Cl_2$ (10 mL) with toluoyl chloride (0.99 mL, 0.750 mmol) in the presence of $SnCl_4$ (1.17 mL, 10.0 mmol) followed by tin complexation with TEA (2.10 mL, 15.0 mmol) and $Bu_2SnCl_2$ (1.52 g, 5.00 mmol) afforded a dark brown residue. Chromatography [alumina, hexanes/$CH_2Cl_2$, (4/1)] afforded a pale green oil (1.03 g, 28%): $^1$H NMR δ 0.69 (t, J=7.2 Hz, 3H), 0.73 (t, J=7.2 Hz, 3H), 1.07–1.70 (m, 12H), 2.44 (s, 3H), 3.77 (s, 3H), 3.89 (s, 3H), 5.54 (s, 1H), 6.16–6.20 (m, 1H), 6.80–6.85 (m, 2H), 6.97–7.02 (m, 2H), 7.07–7.11 (m, 2H), 7.12–7.17 (m, 2H), 7.31 (d, J=8.0 Hz, 2H), 7.82 (d, J=8.0 Hz, 2H), 7.91–7.96 (m, 2H); $^{13}$C NMR δ 13.8, 13.9, 21.8, 24.2, 24.9, 26.2, 26.5, 27.4, 27.5, 29.9, 45.1, 55.5, 55.7, 113.9, 114.2, 115.2, 123.4, 123.9, 129.2, 129.3, 129.4, 130.5, 131.3, 135.3, 135.9, 136.0, 136.8, 142.3, 151.7, 152.1, 158.5, 162.8, 183.7, 184.6.

Dibutyl[5,10-dihydro-1-(4-methoxybenzoyl)-9-(4-methylbenzoyl)-5-(4-methoxyphenyl)dipyrrinato]tin(IV) [3l-Sn(Bu)$_2$]. Following a general procedure described in Method C, 2b (1.93 g, 5.00 mmol) was treated with EtMgBr (30.0 mL, 30.0 mmol, 1.0 M solution in THF) in toluene (20 mL) and then reacted with p-toluoyl chloride (2.00 mL, 15.0 mmol). Following tin complexation with TEA (2.10 mL, 15.0 mmol) and $Bu_2SnCl_2$ (1.52 g, 5.00 mmol) afforded a dark brown residue. Chromatography [alumina, hexanes/$CH_2Cl_2$, (4/1)] afforded a green solid (588 mg, 14%) with satisfactory analytical data (mp, $^1$H NMR spectrum, and elemental analysis).

Dibutyl[5,10-dihydro-1-(4-methylbenzoyl)-9-(4-iodobenzoyl)-5-(pentafluorophenyl)dipyrrinato]tin(IV) [3n-Sn(Bu)$_2$]. Following a general procedure described in Method B, but at 250 mM concentration due to the poor solubility of 2f, a reaction of 2f (2.15 g, 5.00 mmol) in $CH_2Cl_2$ (20 mL) with 4-iodobenzoyl chloride (2.00 g, 7.50 mmol) in the presence of $SnCl_4$ (1.17 mL, 10.0 mmol) followed by tin complexation with TEA (2.10 mL, 15.0 mmol) and $Bu_2SnCl_2$ (1.52 g, 5.00 mmol) afforded a dark purple residue. Chromatography (silica, $CH_2Cl_2$) afforded a purple solid (2.54 g, 57%): mp 69–70° C. (dec.); $^1$H NMR δ 0.68–0.79 (m, 6H), 1.16–1.27 (m, 4H), 1.34–1.46 (m, 4H), 1.55–1.65 (m, 4H), 2.45 (s, 3H), 6.08 (d, J=4.0 Hz, 2H), 6.12

(s, 1H), 7.05 (d, J=4.0 Hz, 1H), 7.12 (d, J=4.0 Hz, 1H), 7.31 (d, J=8.0 Hz, 2H), 7.63 (d, J=8.0 Hz, 2H), 7.80–7.89 (m, 4H); 13.27, 13.33, 21.4, 24.0, 24.3, 25.8, 25.9, 26.7, 27.0, 33.7, 98.7, 113.8, 114.0, 117.1 (m), 123.3, 123.5, 128.91, 128.93, 130.3, 131.5, 134.2, 134.9, 135.2, 136.1 (m), 136.6, 137.4, 138.1, 138.7 (m), 141.5 (m), 142.3, 143.4 (m), 145.9 (m), 146.7, 147.6, 183.6, 184.7.

Synthesis of 8-[Sn(Bu)$_2$]$_2$. A THF solution of 1 M EtMgBr (5.00 mL, 5.00 mmol) was added slowly to a tap-water-cooled flask containing a suspension of 1,4-bis (dipyrromethane-5-yl)benzene (7, 183 mg, 0.500 mmol) in toluene (30 mL) under argon. An exothermic reaction with gas evolution ensued. The resulting green solution was stirred for 30 min at room temperature. Then a solution of 3,5-di-tert-butylbenzoyl chloride (632 mg, 2.50 mmol) in toluene (3.0 mL) was added over 5 min. The mixture was stirred for an additional 10 min. The reaction was quenched by adding saturated aqueous NH$_4$Cl (50 mL) and ethyl acetate (50 mL). The organic phase was washed successively with water, brine and then dried (Na$_2$SO$_4$). The solvent was removed under reduced pressure. The resulting residue was dissolved in CH$_2$Cl$_2$ (20 mL). TEA (367 µL, 5.00 mmol) and dibutyltin dichloride (303 mg, 1.00 mmol) were added and the mixture was stirred at room temperature for 30 min. The reaction mixture was concentrated. Flash column chromatography (silica, 6.0×7 cm, CH$_2$Cl$_2$/hexanes=5:1) removed the black material and gave a blue eluent (400 mL). The blue eluent was concentrated to dryness. The residue was dissolved in CH$_2$Cl$_2$, then MeOH was added causing formation of a precipitate. The precipitate was collected by filtration. The filtrate was concentrated and precipitated. This process was repeated once more. The precipitates were combined affording the target material as a pale blue solid (165 mg, 20%): mp>270° C.; $^1$H NMR δ 0.66–0.76 (m, 12H), 1.04–1.76 (m, 96H), 5.55 (s, 2H), 6.19 (d, J=3.9 Hz, 4H), 7.01 (d, J=3.9 Hz, 4H), 7.14 (s, 4H), 7.61 (m, 4H), 7.70 (m, 8H); $^{13}$C NMR δ 13.8, 13.9, 24.1, 25.4, 26.3, 26.5, 27.4, 27.5, 31.6, 35.2, 45.4, 115.3, 123.5, 124.0, 126.0, 128.5, 136.4, 137.3, 142.7, 151.1, 151.4, 185.9; Anal. Calcd for C$_{100}$H$_{134}$N$_4$O$_4$Sn$_2$: C, 70.92; H, 7.98; N, 3.31. Found: C, 70.97; H, 7.98; N, 3.33.

1,9-Dimesitoyl-5-mesityldipyrromethane (3c). A solution of 5-mesityldipyrromethane (1e) (0.99 g, 3.75 mmol) in 1,2-dichloroethane (7.5 mL) was treated with mesitoyl chloride (2.055 g, 11.25 mmol) followed by SnCl$_4$ (0.85 mL, 7.5 mmol) at room temperature. After 45 min, the reaction was quenched with aqueous saturated NaHCO$_3$ and filtered (through a Buchner funnel using Whatman filter paper) and the filtered material was washed with CHCl$_3$. The filtrate was taken in a separating funnel and the organic layer was separated. The aqueous layer was extracted with CHCl$_3$. The combined organic layer was dried (Na$_2$SO$_4$) and concentrated to afford a dark solid. Chromatography [silica, CHCl$_3$/ethyl acetate (95:5)] followed by trituration with hexanes afforded a yellow powder (0.894 g, 43%): mp 263–265° C.; $^1$H NMR δ 2.09 (s, 6H), 2.16 (s, 12H), 2.31 (s, 6H), 2.32 (s, 3H), 5.98–6.02 (m, 1H), 6.09–6.14 (m, 2H), 6.40–6.46 (m, 2H), 6.86 (s, 4H), 6.91 (s, 2H), 9.20 (brs, 2H); $^{13}$C NMR 14.1, 19.3, 20.7, 20.8, 21.1, 22.7, 31.6, 39.0, 110.6, 120.4, 128.1, 130.8, 132.0, 132.2, 134.41, 134.44, 136.6, 137.3, 137.6, 138.2, 139.5, 188.7; FAB-MS obsd 557.3191, calcd 557.3168 [(M+H)+] (C$_{38}$H$_{40}$N$_2$O$_2$); Anal. Calcd for C$_{38}$H$_{40}$N$_2$O$_2$: C, 81.98, H, 7.24, N, 5.03. Found: C, 81.12, H, 7.67, N, 4.72.

1,9-Bis(trifluoroacetyl)-5-phenyldipyrromethane (3i). A solution of 1a (222 mg, 1.00 mmol) in dry CH$_2$Cl$_2$ (10.0 mL) was treated with 4-(N,N-dimethylamino)pyridine (DMAP, 24 mg, 0.20 mmol, 0.20 equiv) and (CF$_3$CO)$_2$O (353 µL, 2.50 mmol, 2.5 equiv) at room temperature. After 10 min, TLC analysis (silica, CH$_2$Cl$_2$) indicated complete consumption of the starting materials. The reaction mixture was washed with aqueous NaHCO$_3$, H$_2$O and dried (Na$_2$SO$_4$). Chromatography [silica, CH$_2$Cl$_2$→CH$_2$Cl$_2$/methanol (95:5)] afforded a gray solid (409 mg, 98%): mp 149–151° C.; $^1$H NMR δ 5.60 (s, 1H), 6.14–6.16 (m, 2H), 7.14–7.16 (m, 2H), 7.32–7.42 (m, 5H), 10.48 (br s, 2H); $^{13}$C NMR δ 44.8, 123.6, 125.7, 128.21, 128.51, 129.25, 138.0, 144.8, 170.1 (q); FAB-MS obsd 414.0814, calcd 414.0803. Anal. Calcd for C$_{19}$H$_{12}$F$_6$N$_2$O$_2$: C, 55.08; H, 2.92; N, 6.76. Found: C, 55.31; H, 2.92; N, 6.87.

Decomplexation of a Diacyldipyrromethane-Sn Complex. Exemplified for 1,9-Bis(4-methylbenzoyl)-5-phenyldipyrromethane (3a). A suspension of 3a-Sn(Bu)$_2$ (345 mg, 0.500 mmol, 100 mM) in hexanes (5 mL) was treated with TFA (116 µL, 1.50 mmol, 300 mM) for 10 min at room temperature. The reaction mixture was subjected to flash column chromatography (silica, 6.0×5 cm, eluent: hexanes/ethyl acetate (2/1), 300 mL) to afford a pale red eluent. The eluent was concentrated and the residue was dissolved in Et$_2$O (50 mL). Hexanes (50 mL) was added, affording a precipitate. The precipitate was collected by filtration. The filtrate was concentrated and the precipitation method was repeated twice. The precipitates were combined affording the target material as a colorless solid (218 mg, 95%) with satisfactory analytical data (mp, $^1$H NMR spectrum, and elemental analysis).

1,9-Diformyl-5-phenyldipyrromethane (3b). Following the general procedure, a solution of 3b-Sn(Bu)$_2$ (255 mg, 0.50 mmol) in CH$_2$Cl$_2$ (5.0 mL) was treated with TFA (116 µL, 1.50 mmol, 3 equiv) for 10 min at room temperature. Chromatography [silica, CH$_2$Cl$_2$/ethyl acetate (9:1)] afforded a brown solid. Precipitation from ether/hexanes afforded a colorless solid (136 mg, 98%) with satisfactory characterization data ($^1$H NMR spectrum, mp 166–168° C.).

1-(4-Methylbenzoyl)-9-(4-iodobenzoyl)-5-(pentafluorophenyl)dipyrromethane (3o). Following a general procedure described for the decomplexation of 3a-Sn(Bu)$_2$, treatment of 3o-Sn(Bu)$_2$ (891 mg, 1.00 mmol) with TFA (0.230 mL, 3.00 mmol) for 30 min, afforded a colorless solid (539 mg, 82%): mp 152–153° C.; $^1$H NMR δ 2.40 (s, 3H), 6.02–6.08 (m, 2H), 6.18 (s, 1H), 6.50–6.62 (m, 2H), 7.22 (d, J=8.0 Hz, 2H), 7.48 (d, J=8.0 Hz, 2H), 7.68 (d, J=8.0 Hz, 2H), 7.77 (d, J=8.0 Hz, 2H), 11.45 (brs, 2H); $^{13}$C NMR 21.6, 33.6, 99.5, 110.6, 110.8, 113.9, 120.3, 120.6, 128.9, 129.7, 130.9, 131.0, 131.4, 135.1, 135.9, 136.9, 137.1, 137.4, 139.1 (m), 139.6 (m), 142.2 (m), 142.8 (m), 143.9 (m), 146.4 (m), 183.5, 184.4.

Direct Porphyrin Formation from 3a-Sn(Bu)$_2$. Synthesis of 5,15-Bis(4-methylphenyl)-10,20-diphenylporphyrin (9). A solution of 3a-Sn(Bu)$_2$ (276 mg, 0.400 mmol) in dry THF/MeOH (15 mL, 10:1) was treated with NaBH$_4$ (303 mg, 8.00 mmol, 20 eq) in small portions with rapid stirring at room temperature. TLC analysis after 2 h [silica, hexanes/ethyl acetate (3:1)] indicated incomplete reduction. Therefore, an additional amount of NaBH$_4$ ((303 mg, 8.00 mmol, 20 eq) was added likewise. After another 2 h, TLC analysis showed complete reduction of 3a-Sn(Bu)$_2$. The reaction was quenched by careful addition of saturated aq NH$_4$Cl. The reaction mixture was extracted with CH$_2$Cl$_2$, dried (K$_2$CO$_3$) and concentrated, affording 3a-diol as a slightly yellow foam-like solid. The freshly prepared 3a-diol was condensed with 1a (89 mg, 0.40 mmol) in CH$_2$Cl$_2$ (160 mL) under catalysis with Yb(OTf)$_3$ (317 mg, 0.512 mmol, 3.2 mM) at room temperature. After 30 min, DDQ (272 mg, 1.20 mmol, 3 eq) was added and the reaction mixture was stirred for 1 h at room temperature. The reaction mixture was then neutralized with TEA and filtered through a pad of silica gel (eluted with $CH_2Cl_2$). The first fraction was collected and concentrated. The residue was washed with methanol (sonicated, filtered and dried), affording a purple solid (75 mg, 29%): The analytical data ($^1$H NMR, LD-MS, UV-Vis and fluorescence) were consistent with those reported in the literature. B. J. Littler, et al., *J. Org. Chem.* 1999, 64, 2864–2872. The duplicate reaction afforded the similar yield of product (71 mg, 28%).

Results and Discussion

1. Tin Complexation Studies.

Substrate Selectivity. Kitamura and Yamashita reported that 1,9-dicarbomethoxy-3,7-dibromodipyrromethane (4) reacted with dibutyltin dichloride ($Bu_2SnCl_2$) in the presence of TEA at room temperature to give the corresponding dibutyltin complex 4-Sn(Bu)$_2$ (Scheme 2). C. Kitamura, et al., *J. Chem. Soc., Perkin Trans.* 1 1997, 1443–1447. We repeated this reaction with 1,9-bis(4-methylbenzoyl)-5-phenyldipyrromethane (3a) and obtained the corresponding tin complex 3a-Sn(Bu)$_2$ in 90% yield (Scheme 3). The tin complex was stable to water, was readily isolated by flash chromatography on silica, was easily crystallized from ethyl ether/methanol, and gave satisfactory purity upon elemental analysis.

Scheme 2

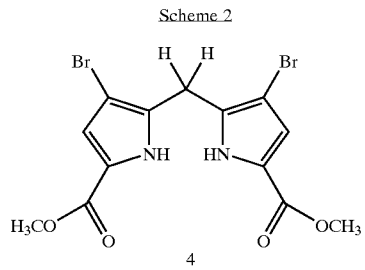

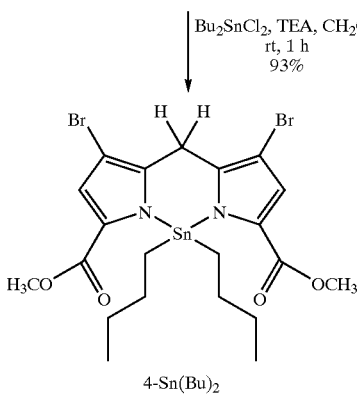

4-Sn(Bu)$_2$

To explore the selectivity of tin complexation of a diacyldipyrromethane, the following control experiments (Scheme 3) were carried out. (1) Treatment of the dipyrromethane 1a (lacking the 1,9-diacyl groups) with $Bu_2SnCl_2$ and TEA in $CH_2Cl_2$ did not give the corresponding tin complex 1a-Sn(Bu)$_2$. (2) Treatment of the monoacyl dipyrromethane 2a under the same conditions did not produce any tin complex 2a-Sn(Bu)$_2$. (3) Treatment of the 1,8-diacyldipyrromethane 5 under the same conditions did not give the corresponding tin complex 5-Sn(Bu)$_2$. (4) Treatment of a mixture (1:1 molar ratio) of the dipyrromethane 1a and the diacyl dipyrromethane 3a under the same conditions as in (1) gave exclusively the diacyldipyrromethane tin complex 3a-Sn(Bu)$_2$. The successful complexation of a 1,9-diacyldipyrromethane and the failure with a dipyrromethane, monoacyldipyrromethane and 1,8-diacyldipyrromethane (an isometric analog of 1,9-diacyldipyrromethane) indicated that tin complexation could be useful in a purification procedure.

Scheme 3

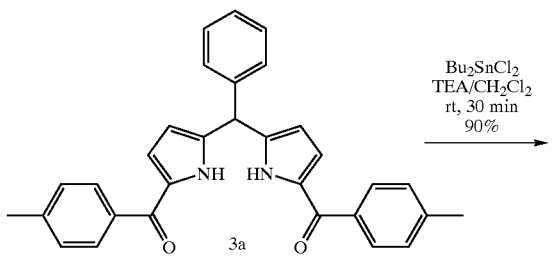

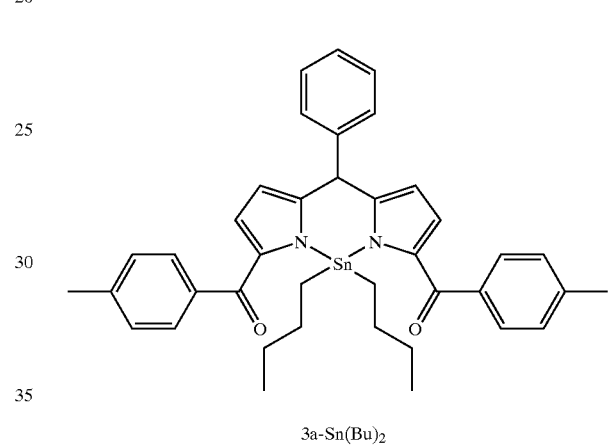

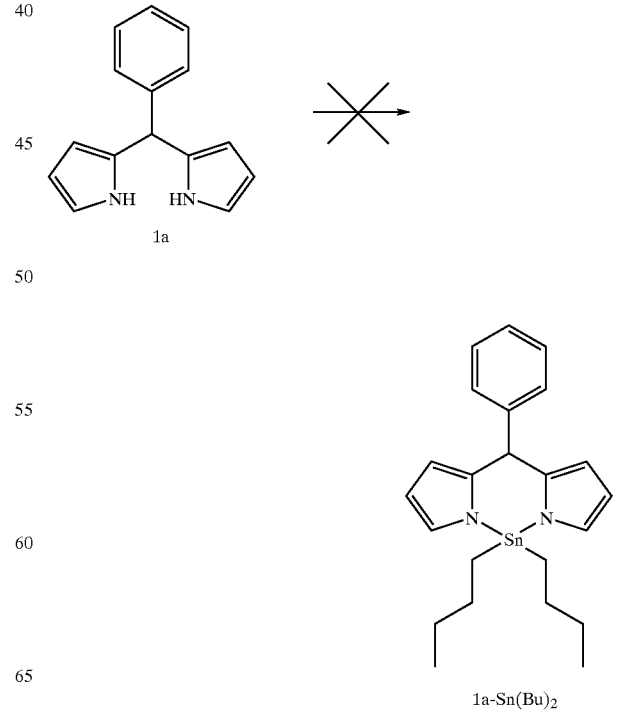

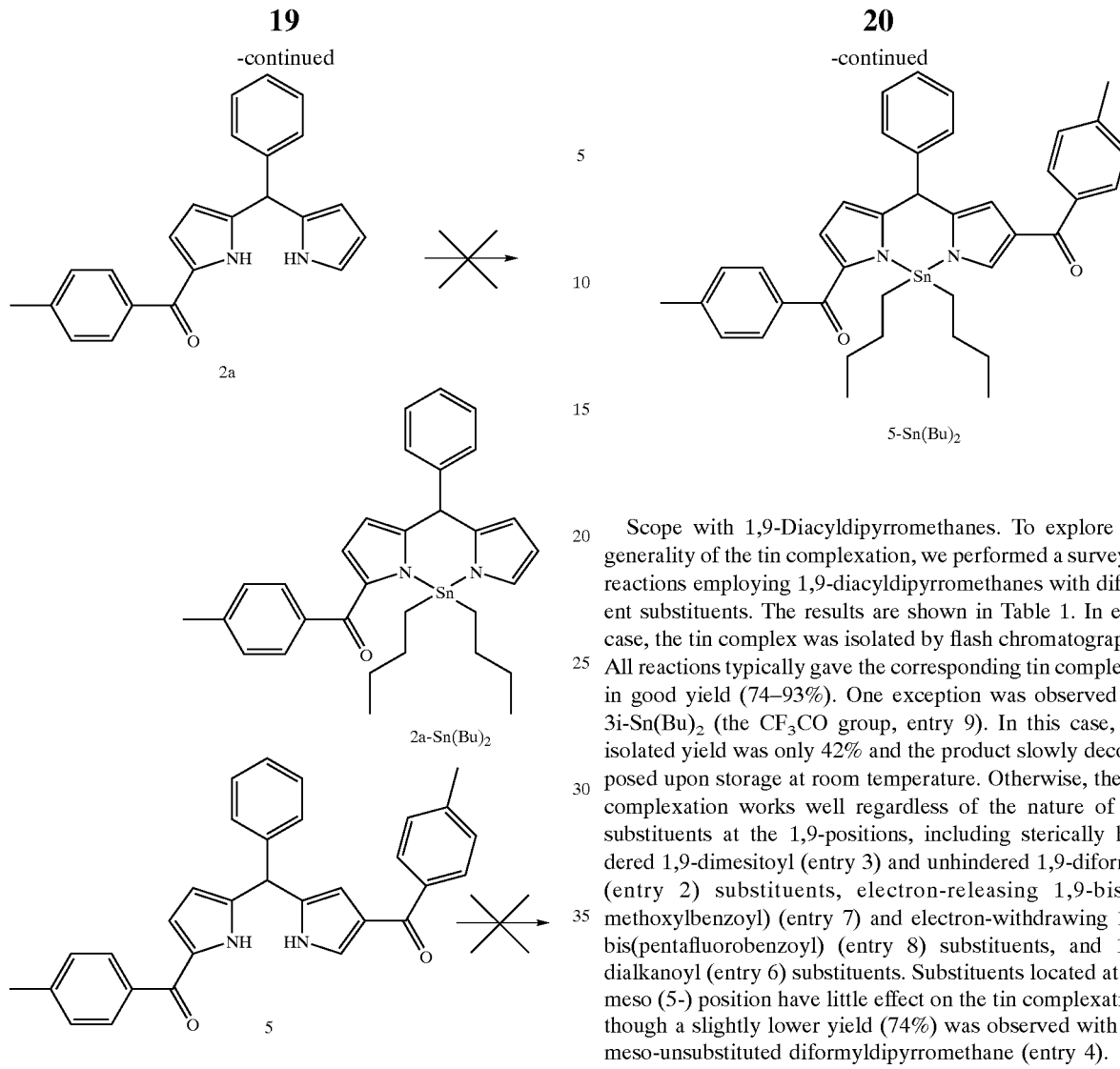

Scope with 1,9-Diacyldipyrromethanes. To explore the generality of the tin complexation, we performed a survey of reactions employing 1,9-diacyldipyrromethanes with different substituents. The results are shown in Table 1. In each case, the tin complex was isolated by flash chromatography. All reactions typically gave the corresponding tin complexes in good yield (74–93%). One exception was observed for 3i-Sn(Bu)$_2$ (the CF$_3$CO group, entry 9). In this case, the isolated yield was only 42% and the product slowly decomposed upon storage at room temperature. Otherwise, the tin complexation works well regardless of the nature of the substituents at the 1,9-positions, including sterically hindered 1,9-dimesitoyl (entry 3) and unhindered 1,9-diformyl (entry 2) substituents, electron-releasing 1,9-bis(4-methoxylbenzoyl) (entry 7) and electron-withdrawing 1,9-bis(pentafluorobenzoyl) (entry 8) substituents, and 1,9-dialkanoyl (entry 6) substituents. Substituents located at the meso (5-) position have little effect on the tin complexation, though a slightly lower yield (74%) was observed with the meso-unsubstituted diformyldipyrromethane (entry 4).

TABLE 1

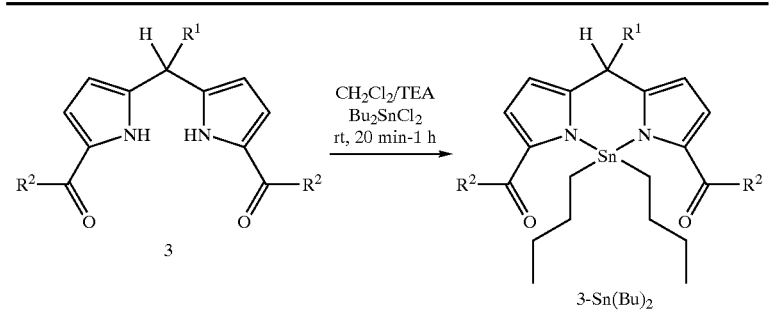

| Entry | R$^1$ | R$^2$ | Product (Yield) |
|---|---|---|---|
| 1 (a) | phenyl | 4-methylphenyl | 3a-Sn(Bu)$_2$(90%) |
| 2 (b) | phenyl | H | 3b-Sn(Bu)$_2$(86%) |

TABLE 1-continued
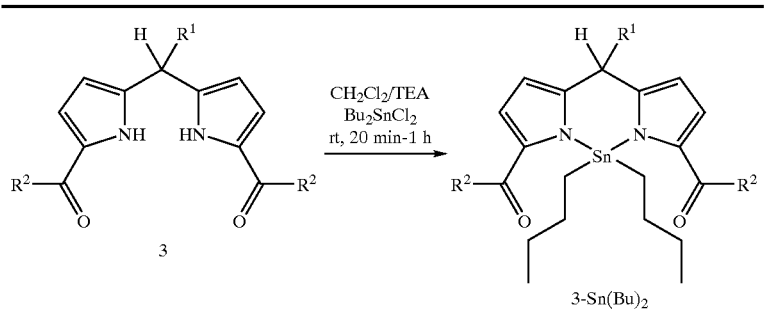
| Entry | R¹ | R² | Product (Yield) |
|---|---|---|---|
| 3 (c) | 2,4,6-trimethylphenyl | 2,4,6-trimethylphenyl | 3c-Sn(Bu)$_2$ (90%) |
| 4 (d) | H | H | 3d-Sn(Bu)$_2$ (74%) |
| 5 (e) | H | 4-methylphenyl | 3e-Sn(Bu)$_2$ (85%) |
| 6 (f) | n-pentyl | n-pentyl | 3f-Sn(Bu)$_2$ (93%) |
| 7 (g) | phenyl | 4-OMe-phenyl | 3g-Sn(Bu)$_2$ (91%) |
| 8 (h) | pentafluorophenyl | pentafluorophenyl | 3h-Sn(Bu)$_2$ (87%) |
| 9 (i) | phenyl | CF$_3$ | 3i-Sn(Bu)$_2$ (42%)[a] |
| 10 (j) | 2,4,6-trimethylphenyl | 3-iodophenyl | 3j-Sn(Bu)$_2$ (89%) |

TABLE 1-continued

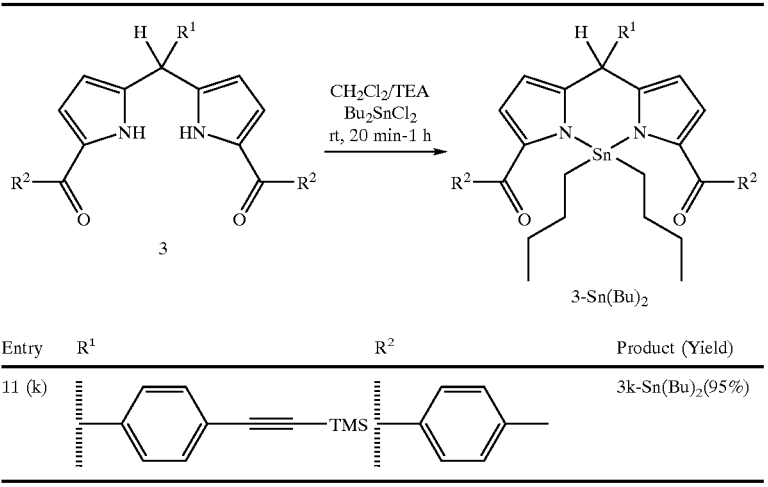

| Entry | R¹ | R² | Product (Yield) |
|---|---|---|---|
| 11 (k) | ⋮—⟨⟩—≡—TMS | ⋮—⟨⟩—  | 3k-Sn(Bu)₂(95%) |

ᵃThe product decomposed slowly upon storage at room temperature.

The reaction of diacyldipyrromethane 3a with diphenyltin dichloride ($Ph_2SnCl_2$) afforded the complex 3a-Sn(Ph)₂ in 91% yield, illustrating the generality of the complexation process (Scheme 4).

Scheme 4

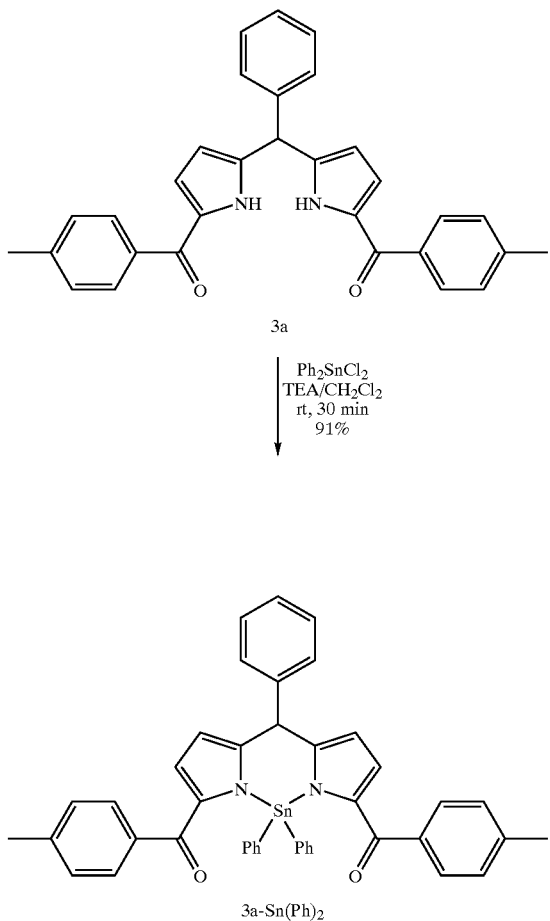

Characterization. The diacyldipyrromethane-tin complexes are stable to water and routine handling. The stability to water distinguishes these complexes from alkyltin-pyrroles, such as N-(tributylstannyl)pyrrole, which decomposes upon exposure to water or alcohols. J. C. Pommier, et al., *J. Organomet. Chem.* 1973, 57, 139–153. Unlike diacyldipyrromethanes, the tin-diacyldipyrromethane can easily be crystallized from ethyl ether/methanol and affords satisfactory elemental analysis results. The butyl groups attached to Sn atom give two sets of $^{13}C$ signals for diacyldipyrromethanes that bear a single meso substituent, owing to the different magnetic environment of the two butyl groups (syn or anti with respect to the meso substituent).

X-ray structural analyses were performed on compound 3a-Sn(Bu)₂. The Sn atom is 6-coordinate adopting a highly distorted pseudo-octahedral geometry, with the O1—Sn1—O2 angle having a value of 135.97(7)° and the O1—Sn1—N2 angle having a value of 153.36(8)°. The two pyrrole rings are nearly coplanar with a dihedral angle of 16.62(13)°. The Sn—N and Sn—C bond distances are both less than 2.16 Å, while the Sn—O distances are 2.461(2) and 2.488(2) Å for O1 and O2 respectively. These Sn—O distances are both shorter and more symmetric than those reported by Kitamura and Yamashita of the 1,9-diester-substituted dipyrromethane [4-Sn(Bu)₂]. C. Kitamura, et al., *J. Chem. Soc., Perkin Trans.* 1 1997, 1443–1447.

The facile formation of the tin complex of the compound shown in Scheme 2 was attributed by Kitamura and Yamashita to the presence of two electron-withdrawing groups per pyrrole unit. The results we have obtained indicate that the presence of an acyl unit at each α-position is necessary and sufficient to give a stable tin complex. The acidity constant for the N—H groups of the diacyldipyrromethanes are not known. However, the $pK_a$ value for pyrrole-2-carboxaldehyde (N—H dissociation) is estimated to be 15, compared with a value of 17.5 for pyrrole itself. M. H. Limage, et al., *Compt. Rend. Serie B* 1975, 280, 601–603; G. Yagil, *Tetrahedron* 1967, 23, 2855–2861. The stability of the tin complexes of the 1,9-diacyldipyrromethanes, and the failure of the 1,8-diacyldipyrromethane to give a stable tin complex, indicates that the presence of carbonyl groups that coordinate to the Sn atom are essential to give a stable complex. Indeed, the X-ray crystal structure obtained showed an essential planar ligand structure encompassing the two pyrrolic N atoms, the two carbonyl groups, and the Sn atom.

Tin Complexation as a Purification Aid. The following features make tin complexation suitable for the separation of the diacyldipyrromethane products from the diacylation reaction: (1) The tin complex is less polar than the corresponding diacyldipyrromethane precursor. A short silica gel column is sufficient for the purification, thereby minimizing the laborious chromatographic process and consuming less solvent. (2) The tin complex has greater solubility in common organic solvents (such as $CHCl_3$, $CH_2Cl_2$, THF and hexanes) than the corresponding diacyldipyrromethane precursor. (3) Unlike diacyldipyrromethanes, the tin-diacyldipyrromethane can easily be crystallized from ethyl ether/methanol and affords satisfactory elemental analysis results. (4) Treatment of the diacyldipyrromethane tin complex with silica gel overnight does not result in decomplexation. (5) Treatment of the diacyldipyrromethane tin complex with acid (such as TFA) usually results in recovery of the corresponding diacyldipyrromethane in high yield (~90%). (6) The monoacyldipyrromethane and the isomeric 1,8-diacyldipyrromethane do not give a tin complex.

We applied the tin-complexation approach to a crude reaction mixture obtained from the attempted diacylation of 5-phenyldipyrromethane (1a) using EtMgBr and p-toluoyl chloride. The mixture obtained following acylation was quenched with aqueous $NH_4Cl$ and the organic layer was separated and concentrated to dryness. The residue was dissolved in $CH_2Cl_2$ or $ClCH_2CH_2Cl$ at room temperature and then treated with TEA and dibutyltin dichloride. The selective tin complexation of the diacyldipyrromethane took place in each solvent. Purification of the diacyldipyrromethane-Sn complex was achieved by silica-pad filtration using hexanes to elute the diacyldipyrromethane-Sn complex. The crude product was dissolved in $Et_2O$ and the ethereal solution was treated with methanol, affording the diacyldipyrromethane-Sn complex as a pale yellow precipitate in 38% yield from the starting dipyrromethane. The refined purification procedure is shown in Scheme 5. The tin complexation approach can be used with diacyldipyrromethanes prepared directly by diacylation of a dipyrromethane or by the acylation of a monoacyldipyrromethane (vide infra).

Scheme 5

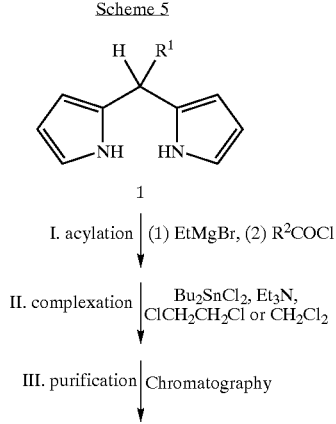

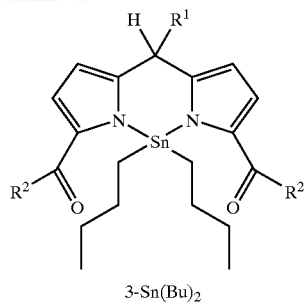

3-Sn(Bu)$_2$

An alternative means for isolation of the 1,9-diacyldipyrromethane is to use a catch-and-release strategy, where the tin dichloride reagent is incorporated in an insoluble polymeric resin. Examples of such resins are known where the tin dichloride unit is located on a pendant group on a cross-linked polymer such as polystyrene. N. M. Weinshenker, et al., *J. Org. Chem.* 1975, 40, 1966–1971; F. A. G. Mercier, et al., *Organometallics* 2001, 20, 958–962. In one case the tin atom bears two alkyl groups and two chlorides, while in a second case the tin atom bears one p-phenylene group, one butyl group, and two chloride atoms. In yet a third case, the tin atom bears one p-phenylene group, one butyl group, and two iodide atoms. The loading of the polymer with tin and the cross-linking can be varied in standard ways. A loading of 2 mmol of tin per gram of resin is typical. The attractive feature of the immobilized tin dichloride unit in the polymeric resin is that the crude reaction mixture can be treated with the resin and an appropriate base in a suitable solvent (e.g., $CH_2Cl_2$, 1,2-dichloroethane, toluene, tetrahydrofuran). The mixture is then filtered, whereupon the filtered material consists of the resin containing the diacyldipyrromethane as the tin complex in the resin. The filtered material is then washed in the standard way to give the byproducts in the filtrate. The diacyldipyrromethane can then be released from the resin upon treatment with an acid as done for the tin complex in solution.

2. Acylation of Dipyrromethanes.

Diacylation with Identical 1,9-Substituents. We investigated conditions encompassing diverse Lewis acids and solvents aimed at the direct acid-catalyzed diacylation of a dipyrromethane. We surveyed the following Lewis acids as potential catalysts for the diacylation of 5-phenyldipyrromethane (1a) with p-toluoyl chloride to give the corresponding 1,9-diacyldipyrromethane 3a: $SbCl_5$, $TiCl_4$, $SnCl_4$, $Sc(OTf)_3$, $Yb(OTf)_3$, $Sm(OTf)_3$, $La(OTf)_3$, $In(OTf)_3$, $Bi(OTf)_3$, $BiCl_3$, $ZnCl_2$, $InCl_3$, and $BF_3.O(Et)_2$ in various solvents ($ClCH_2CH_2Cl$, $MeNO_2$, $CH_2Cl_2$, THF, MeCN, toluene or 1,2-dichlorobenzene) at room temperature. Among the Lewis acids, $SbCl_5$ or $SnCl_4$ was effective in $ClCH_2CH_2Cl$, $CH_2Cl_2$, or $MeNO_2$. However, decomposition and polymerization of the starting dipyrromethane appeared to compete with the acylation. In the presence of $LiClO_4$ as co-catalyst, $Sc(OTf)_3$, $Yb(OTf)_3$, $Sm(OTf)_3$, $La(OTf)_3$, and $In(OTf)_3$ showed moderate results in $MeNO_2$. However, because the diacylation reaction is slow with these catalysts (requring several hours), decomposition of the dipyrromethane (presumably by HCl formed in the reaction) competes with the acylation. Thus, an excess of the acid chloride was required for the diacylation reaction. We found that the hydrolysis of the acid chloride is faster in $MeNO_2$ than in $ClCH_2CH_2Cl$. The Lewis acids $InCl_3$, $ZnCl_2$, and BF$_3$.O(Et)$_2$ were virtually useless for the diacylation in any solvent. When THF, MeCN or toluene was used as solvent, the acylation gave trace amounts of the target diacyldipyrromethane, regardless of catalyst. The use of SbCl$_5$ in ClCH$_2$CH$_2$Cl gave the diacyldipyrromethane in good yields (~60% yield at 50 mM concentration and 40~50% at 100 mM concentration). On the other hand, with SnCl$_4$ (a milder catalyst than SbCl$_5$) in ClCH$_2$CH$_2$Cl, the diacyldipyrromethane was obtained in ~40% yield over the concentration range of 50~200 mM. In a reaction using 0.2 equiv of Lewis acid [SbCl$_5$, SnCl$_4$, or Sc(OTf)$_3$/LiClO$_4$] in ClCH$_2$CH$_2$Cl, the acylation was slow and decomposition of the dipyrromethane was the dominant process.

We believe that the HCl formed during the reaction led to decomposition of the dipyrromethane resulting in the lower yields of diacyldipyrromethane. Thus, we thought use of organic or inorganic bases may scavenge the HCl and should facilitate the diacylation. Several bases [TEA, DIEA, DMAP, proton sponge, 2,6-di-tert-butylpyridine (DTBP), K$_2$CO$_3$, basic alumina, and weak-base ion-exchange resin] were used as acid scavengers. In the presence of excess base, the reaction mixture turned green before the addition of acid chloride. When acid chloride was added to the green solution, the acylation did not occur. In the presence of a small excess of base, the acylation proceeded. However, a small excess of base did not maintain the basic reaction conditions; thus, the yield of target diacyldipyrromethane was decreased further than that with no base present. Taken together, it is clear that bases examined inhibit the acylation reaction. We have also examined the following compounds: sodium 2-ethylhexanoate, sodium acetate, sodium 1-adamantane acetate, sodium 9-anthracene carboxylate, sodium trimethyl acetate as acid-scavengers. However, the sodium carboxylates react with the acid chloride affording mixed-acid anhydrides, which in turn result in undesired diacyldipyrromethanes. Highly hindered sodium carbxylates such as sodium 1-adamantane acetate, sodium 9-anthracene carboxylate or sodium trimethyl acetate did not result in an undesired diacyldipyrromethane, but also did not facilitate the diacylation. Trimethoxypropylsilane and methyl trimethylsilyl dimethylketene acetal (MTDA) were also examined as HCl scavengers, but no improvement in the yield of the target diacyldipyrromethane was obtained.

In general, the acylation conditions cause a competition between acylation and decomposition of the dipyrromethane. While some conditions were identified that provide an appropriate balance between acylation and decomposition, none was of broad scope for diverse dipyrromethanes, which we attributed to the sensitivity of the dipyrromethane to acidic conditions. We concluded that the method affording the broadest scope for the synthesis of diacyldipyrromethanes employs the Grignard-mediated diacylation followed by tin complexation of the crude reaction mixture to isolate the diacyldipyrromethane.

During the course of this work, Gryko et al. reported a method for the 1,9-diacylation of a dipyrromethane that entails conversion of an acid chloride to the N-acylmorpholide derivative. D. T. Gryko, et al., *J. Porphyrins Phthalocyanines* 2003, 7, 239–248. The latter is employed in a Vilsmeier acylation method. In particular, the N-acylmorpholide (10 mmol) is treated with excess POCl$_3$ (20 mmol) and the mixture is added to the dipyrromethane (2.5 mmol). After heating and workup by neutralizing the mixture, aqueous organic extraction, chromatography, and crystallization, the diacyldipyrromethane is obtained. This method of acylation also would benefit by the tin complexation strategy, as the tin-diacyldipyrromethanes are readily crystallized and can be isolated from the reaction mixture without extensive chromatography.

Sequential Acylation of the 1,9-Positions. The selective introduction of a single acyl group in a dipyrromethane is achieved by reaction of the dipyrromethane Grignard reagent with a Mukaiyama reagent. This reaction proceeds smoothly at one pyrrole α-position without detectable formation of the diacyldipyrromethane. The original procedure for the synthesis of Mukaiyama reagents employed reaction of equimolar amounts of acid chloride, 2-mercaptopyridine, and TEA (0.67 M each) in THF at room temperature. M. Araki, et al., *Bull. Chem. Soc. Jpn.* 1974, 47, 1777–1780. We developed a slight modification of this method that proceeds in THF (0.5–1.0 M each) in the absence of any base and affords the Mukaiyama reagent (6, Scheme 6) without chromatography. Application of this method to various substrates consistently gave high yields.

SCHEME 6

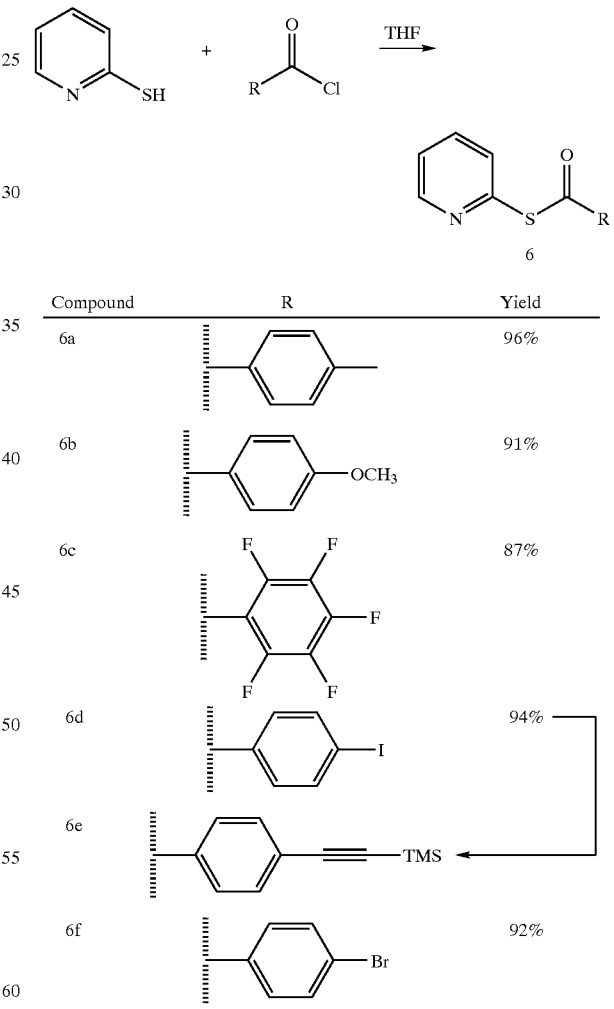

Monoacyl dipyrromethanes 2a–2f were prepared following the general procedure described in the literature with only slight modification for the workup method (Scheme 7). P. Rao et al., *J. Org. Chem.* 2000, 65, 1084–1092.

SCHEME 7

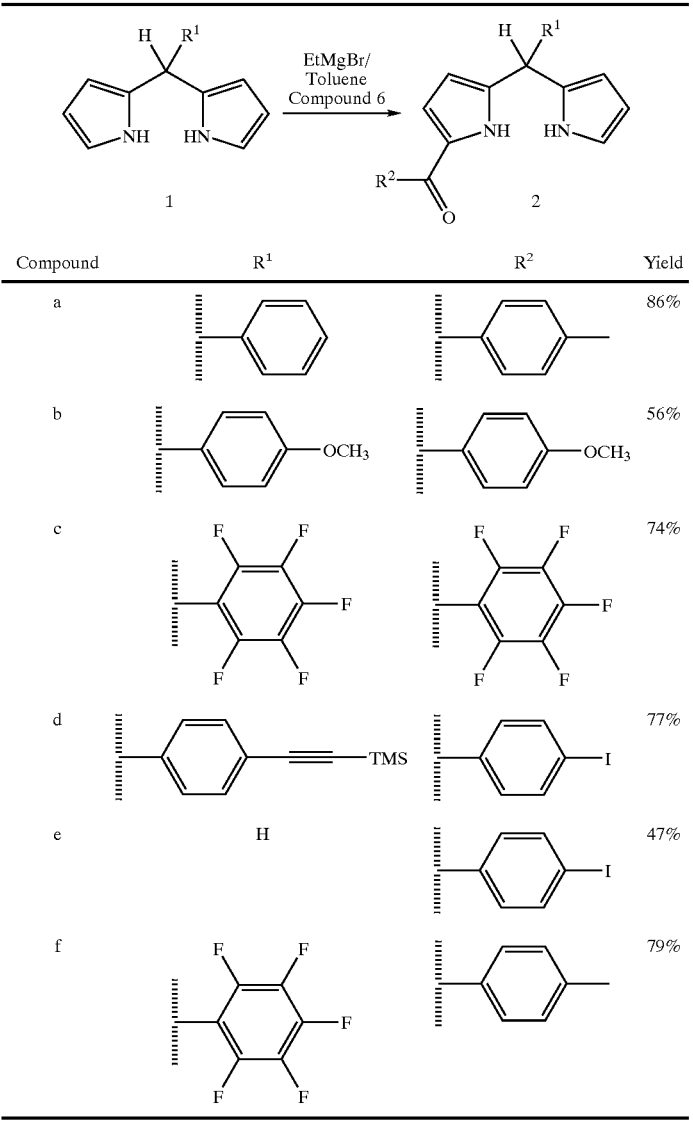

The acylation of a monoacyldipyrromethane has been achieved by reaction with EtMgBr followed by an acid chloride. P. Rao et al., *J. Org. Chem.* 2000, 65, 7323–7344. We investigated two changes in method for the second acylation: (1) Lewis-acid catalyzed acylation of the monoacyldipyrromethane, thereby avoiding Grignard conditions, and (2) use of tin complexation for purification of the diacyldipyrromethane. The best conditions to emerge from the attempted diacylation of a dipyrromethane were investigated for the acylation of a monoacyldipyrromethane. The monoacyldipyrromethane is known to be more stable to acidolysis than the corresponding dipyrromethane. G. R. Geier, III, et al., *J. Porphyrins Phthalocyanines* 2001, 5, 810–823.

The Lewis acids $SbCl_5$, $SnCl_4$, $Sc(OTf)_3$, $Bi(OTf)_3$ were examined for the acylation of the monoacyldipyrromethane 2a with p-toluoyl chloride in $ClCH_2CH_2Cl$ or $MeNO_2$ at room temperature at various concentrations. The major distinctive conditions are summarized in Table 2. The best conditions identified employ the monoacyldipyrromethane at modest concentration (50 mM) in $ClCH_2CH_2Cl$ or $CH_2Cl_2$ with 1.5 equiv of acid chloride and 2.0 equiv of the Lewis acid. Thus, the reaction with either $SbCl_5$ or $SnCl_4$ gave the desired diacyldipyrromethane 3a (~70% yield) as well as an isomeric diacyldipyrromethane 5 (~10% yield).

TABLE 2

Conditions for the acylation of a monoacyldipyrromethane (2a).[a]

| Entry | Acid | [2a][b] | [2a]:[ArCOCl]:[acid] | Solvent | Yield of 3a | Yield of 5 |
|---|---|---|---|---|---|---|
| 1 | $SbCl_5$ | 50 mM | 1.0:1.5:2.0 | DCE[c] | 72% | 8% |
| 2 | $SnCl_4$ | 50 mM | 1.0:1.5:2.0 | DCE | 68% | 12% |
| 3 | $SnCl_4$ | 500 mM | 1.0:1.5:2.0 | DCE | 65% | 14% |
| 4 | $Sc(OTf)_3$ | 1000 mM | 1.0:1.5:0.10 | $MeNO_2$ | 36% | ~10%[d] |
| 5 | $Bi(OTf)_3$ | 1000 mM | 1.0:1.5:0.10 | $MeNO_2$ | Trace | n. o.[e] |

TABLE 2-continued

Conditions for the acylation of a monoacyldipyrromethane (2a).[a]

| Entry | Acid | [2a][b] | [2a]: [ArCOCl]:[acid] | Solvent | Yield of 3a | Yield of 5 |
|---|---|---|---|---|---|---|

[a]Reactions were performed with 0.25 mmol of monoacyldipyrromethane (2a) and the specified amount of p-toluoyl chloride at room temperature and products were isolated by chromatography.
[b]Monoacyldipyrromethane 2a.
[c]1,2-Dichloroethane.
[d]Estimated by TLC analysis.
[e]Not observed.

The structure of 5 was investigated by $^1$H NMR spectroscopy and $^{13}$C NMR spectroscopy, including COSY and NOESY experiments. The $^1$H NMR spectrum of 5 showed four sets of resonances (6.1, 6.5, 6.8, and 7.1 ppm) for the pyrrolic protons, while that of 1,9-diacyldipyrromethane 3a showed only two sets of pyrrolic protons (6.1, 6.8 ppm). COSY and NOESY experiments of 5 showed the presence of coupling between only two sets of protons (6.1, 6.8 ppm) that were assigned to H$^2$, and H$^3$ of the pyrrole ring containing the acyl group at the 1-position as shown previously. C.-H. Lee et al., *Tetrahedron* 1995, 51, 11645–11672. The other two sets of protons (6.5, 7.1 ppm) showed no coupling thereby ruling out the possibility that the second acyl group is located at the 7-position (which has protons at the 8 and 9-positions and would have shown coupling). The two resonances at 6.5 and 7.1 ppm are therefore assigned to H$^7$ and H$^9$, respectively. Thus, the NMR results indicate that the acyl groups in compound 5 are located at the 1 and 8-positions.

Attempts to perform the reaction at higher concentration (entry 3, Table 2) using the same reactant ratios with 500 mM monoacyldipyrromethane gave comparable yields. The requirement for at least stoichiometric quantities of the Lewis acid was regarded as a limitation; however, all attempts to use lesser quantities of Lewis acids resulted in poor yields of diacyldipyrromethane. Even with ratios of monoacyldipyrromethane:acid chloride:acid catalyst of 1.0:1.0:1.0, 1.0:1.5:1.0, or 1.0:1.0:2.0 resulted in unreacted monoacyldipyrromethane. The requirement for stoichiometric or excess quantities of acid catalysts is well known for Friedel-Crafts acylations. The acid-catalyzed acylation of some electron-rich arenes has been reported to proceed with catalytic amounts of acid catalysts such as Sc(OTf)$_3$ or Bi(OTf)$_3$ in polar solvents such as nitromethane. C. Le Roux, Dubac, *J. Synlett* 2002, 181–200; S. Kobayashi, et al., *Chem. Rev.* 2002, 102, 2227–2302; A. Kawada, et al., *Bull Chem. Soc. Jpn.* 2000, 73, 2325–2333. We attempted to employ such conditions (entries 4 and 5) but the yields were quite low. Application of other conditions, such as the Zn-powder mediated acylation of monoacyldipyrromethane under similar conditions reported for the acylation of pyrrole, resulted in extensive decomposition and very little diacyldipyrromethane (11%). J. S. Yadav, et al., *Tetrahedron Lett.* 2002, 43, 8133–8135.

The best conditions for acylation of a monoacyldipyrromethane (using SbCl$_5$ or SnCl$_4$) were applied to a variety of monoacyldipyrromethanes and acid chlorides (Scheme 8). The crude reaction mixtures were subjected to the tin complexation procedure, thereby allowing isolation of each target diacyldipyrromethane as the corresponding tin complex. The results are shown in Scheme 8. Three methods were employed: method A employs SbCl$_5$ with a modest concentration of monoacyldipyrromethane (50 mM); method B employs SnCl$_4$ with a higher concentration of monoacyldipyrromethane (500 mM); and method C employs the standard "Grignard method" (~250 mM). The three methods were compared for formation of 3a-Sn(Bu)$_2$. In general, the acid-catalysis conditions were of sufficient scope to accommodate a variety of substituents in the dipyrromethane or acid chloride unit. In some cases, unreacted monoacyldipyrromethane was observed upon TLC analysis, while in other cases no unreacted monoacyldipyrromethane was observed despite the less than quantitative yield.

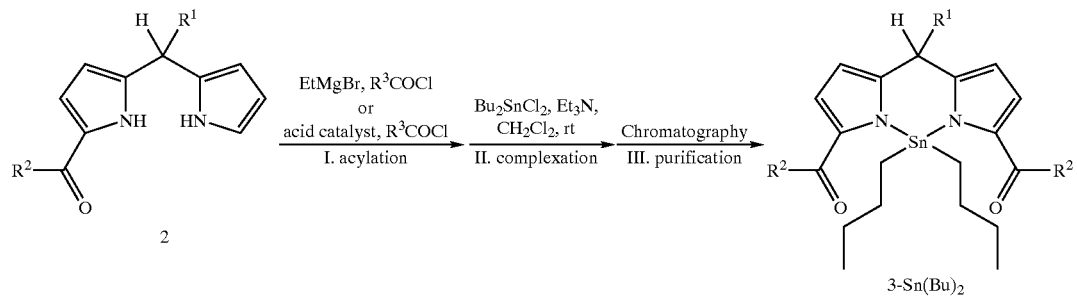

Scheme 8

Scheme 8

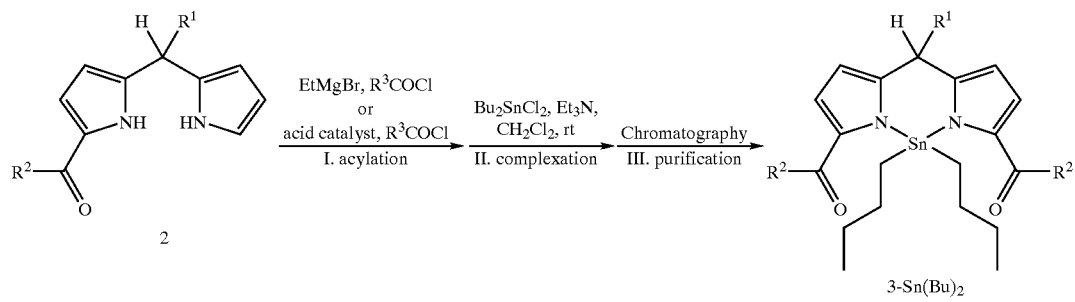

| Entry | R¹ | R² | R³ | Product | Method[a] | Yield |
|---|---|---|---|---|---|---|
| 3 | -C₆H₄-C≡C-TMS | -C₆H₄-I | 3,5-di-t-Bu-C₆H₃ | 3m-Sn(Bu)₂ | B | N.A[b] |
|  |  |  |  |  | C | N.A[b] |
| 4 | C₆F₅ | -C₆H₄-CH₃ | -C₆H₄-I | 3n-Sn(Bu)₂ | B | 57% |

[a]The methods differ only in the conditions for acylation and each method employed the same procedure for tin complexation
Method A: 50 mM monoacyldipyrromethane, 75 mM acid chloride, 100 mM SbCl₅ in dichloromethane.
Method B: 500 mM monoacyldipyrromethane, 750 mM acid chloride, 1000 mM SnCl₄ in 1,2-dichloroethane or dichloromethane.
Method C: 250 mM monoacyldipyrromethane, 1.5 M EtMgBr (1.0 M solution in THF), 750 mM acid chloride in toluene.
[b]Not applicable. Resulted in a mixture of products (observed by TLC analysis and ¹H NMR spectroscopy).

The diacyldipyrromethane-tin complexes were readily isolated, readily crystallized, and were stable on storage for months. The uncomplexed diacyldipyrromethane could be isolated when desired by treatment of the tin complex with a dilute solution of TFA (Scheme 9). The yields for decomplexation ranged from 82–98%.

Scheme 9

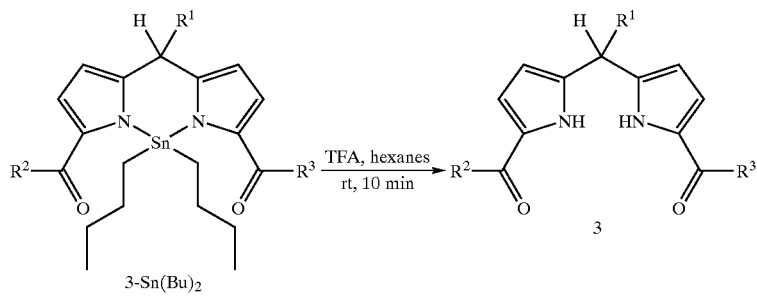

| Entry | R¹ | R² | R³ | Product | Yield |
|---|---|---|---|---|---|
| 1 | -C₆H₅ | -C₆H₄- | -C₆H₄- | 3a | 95% |

-continued

Scheme 9

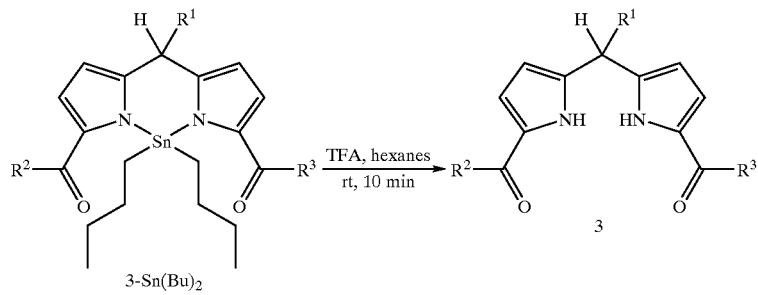

| Entry | R¹ | R² | R³ | Product | Yield |
|---|---|---|---|---|---|
| 2 | phenyl | H | H | 3b | 98% |
| 3 | pentafluorophenyl | 4-(phenyl)phenyl | 4-iodophenyl | 3o | 82% |

Tetraacylation of a Bis(dipyrromethane). 1,4-Bis (dipyrromethan-5-yl)benzene (7) is readily available by reaction of terephthalaldehyde with excess pyrrole. J. S. Yadav, et al., *Tetrahedron Lett.* 2002, 43, 8133–8135; C.-H. Lee, et al., *Tetrahedron* 1994, 50, 11427–11440. Such bis (dipyrromethanes) joined by a p-phenylene linker are potentially valuable components for use in the synthesis of multiporphyrin arrays. Indeed, a variety of bis (dipyrromethan-5-yl)benzene compounds have been used in the synthesis of multiporphyrin arrays, though in each case the dipyrromethanes contained a full complement of substituents at the pyrrolic β-positions and carboxylic acids/ esters at the 1,9-positions. R. G. Khoury, et al., *Tetrahedron* 1999, 55, 6713–6732; R. Paolesse, et al., *J. Am. Chem. Soc.* 1996, 118, 3869–3882; A. Helms, et al., *J. Am. Chem. Soc.* 1992, 114, 6227–6238; J. L. Sessler, et al., *J. Am. Chem. Soc.* 1990, 112, 9310–9329; J. L. Sessler, et al., *Angew. Chem. Int. Ed. Engl.* 1987, 26, 678–680.

We recently developed rational routes to p-phenylene linked multiporphyrin arrays with meso-substituted, β-unbsubstituted porphyrins in distinct metalation states; the routes employed porphyrin-dipyrromethanes and porphyrin-diacyldipyrromethanes. M. Speckbacher, et al., *Inorg. Chem.* 2003, 42, 4322–4337. The ability to employ 7 and derivatives therefrom would provide advantages in these routes. A major limitation, however, stems from the poor solubility of 1,4-bis(dipyrromethan-5-yl)benzene (7) in typical organic solvents. Moreover, prior attempts to prepare the tetraacyl derivative 8 encountered difficult separations owing to incomplete acylation. We addressed the separation problem through use of the tin complexation purification approach (Scheme 10).

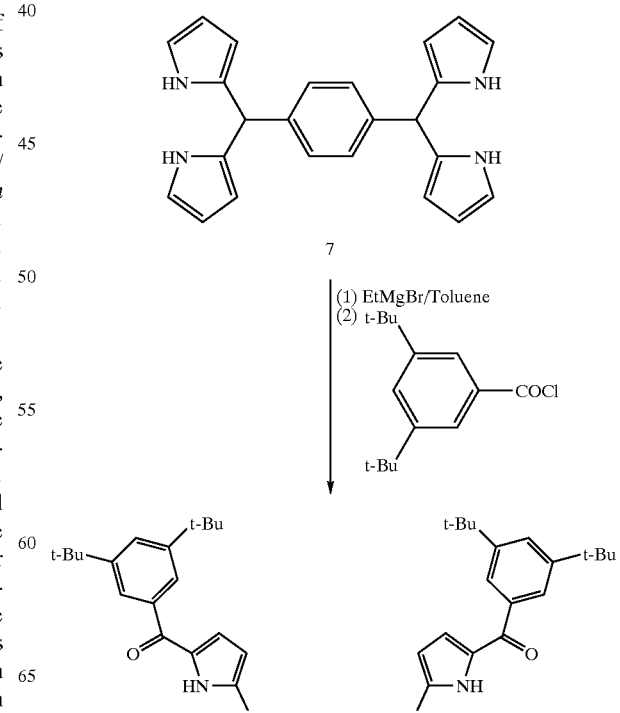

Scheme 10

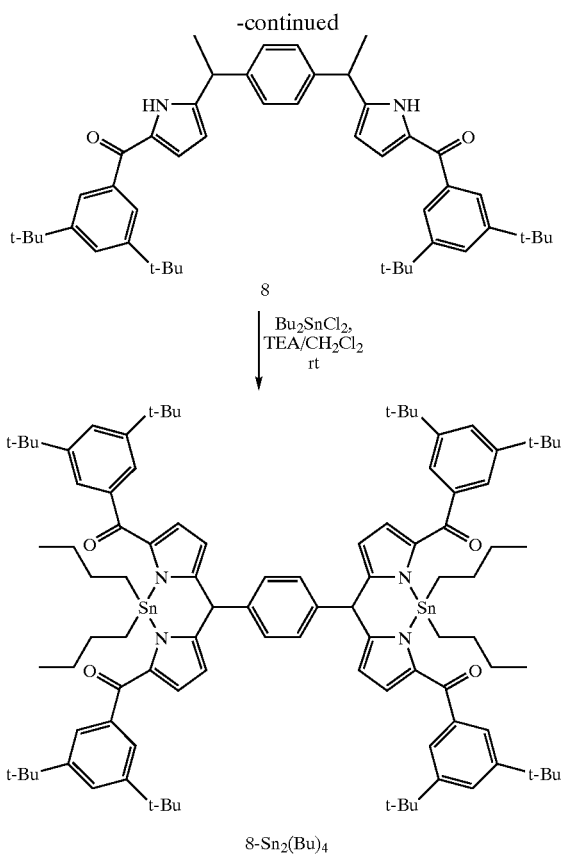

8

Bu₂SnCl₂,
TEA/CH₂Cl₂
rt

8-Sn₂(Bu)₄

A suspension of compound 7 in toluene was treated with EtMgBr followed by addition of 3,5-di-tert-butylbenzoyl chloride, affording several reaction products upon TLC analysis. Workup followed by tin complexation was accomplished in the same manner as for the dipyrromethanes described above. Flash column chromatography followed by precipitation afforded the target compound 8-Sn2(BU)₄ (20%). This compound can be used in the synthesis of p-phenylene-linked multiporphyrin arrays.

3. Direct Synthesis of Porphyrins from Diacyldipyrromethane-Tin Complexes.

It occurred to us that the diacyldipyrromethane-tin complex might be used as a precursor for the synthesis of porphyrins. Thus, we chose to synthesize the porphyrin from 3a-Sn(Bu)₂. Accordingly, the diacyldipyrromethane-tin complex 3a-Sn(Bu)₂ was reduced to the putative dicarbinol derivative (3a-diol) following a standard method for the reduction of diacyldipyrromethanes using NaBH₄ (Scheme 11). We found that the reduction of 3a-Sn(Bu)₂ to the dipyrromethane-dicarbinol 3a-diol took longer (3.5–4 h) than the corresponding reduction of 3a to 3a-diol (40 min–1 h) as observed by TLC analysis. Condensation of 3a-diol [obtained from the reduction of 3a-Sn(Bu)₂] with 1a was carried out using the standard procedure reported in the literature: Yb(OTf)₃ (3.2 mM) in CH₂Cl₂ (2.5 mM) at room temperature followed by oxidation with DDQ. G. R. Geier, III, et al., *J. Porphyrins Phthalocyanines* 2001, 5, 810–823. For comparison, the standard condensation of 3a-diol (resulted from the direct reduction of 3a) and 1a under the same conditions was also performed. The yield of porphyrin over condensation time was assessed by removing a reaction aliquot and oxidizing with DDQ, followed by UV-Vis spectroscopic analysis. The results are shown in FIG. 1: (1) In both cases, the yield of porphyrin peaked at ~15 min (27–29%) and remained nearly constant up to 30 min; (2) No scrambled porphyrin products were observed upon analysis of each crude reaction mixture by LD-MS; (3) No tin porphyrin was observed upon analysis of the crude reaction mixture (absence of m/z=759.5, Sn-9: $C_{46}H_{32}N_4Sn$) by LD-MS. The absence of the tin complexation of the porphyrin from the reaction was further confirmed by $^1$H NMR, UV-Vis, fluorescence and LD-MS analysis of the isolated product 9 from this reaction; (4) The isolated yield of porphyrin 9 from the condensation of 3a-diol [resulted from the reduction of 3a-Sn(Bu)₂] and 1a was 28%, which was consistent with the yield observed spectroscopically.

Scheme 11

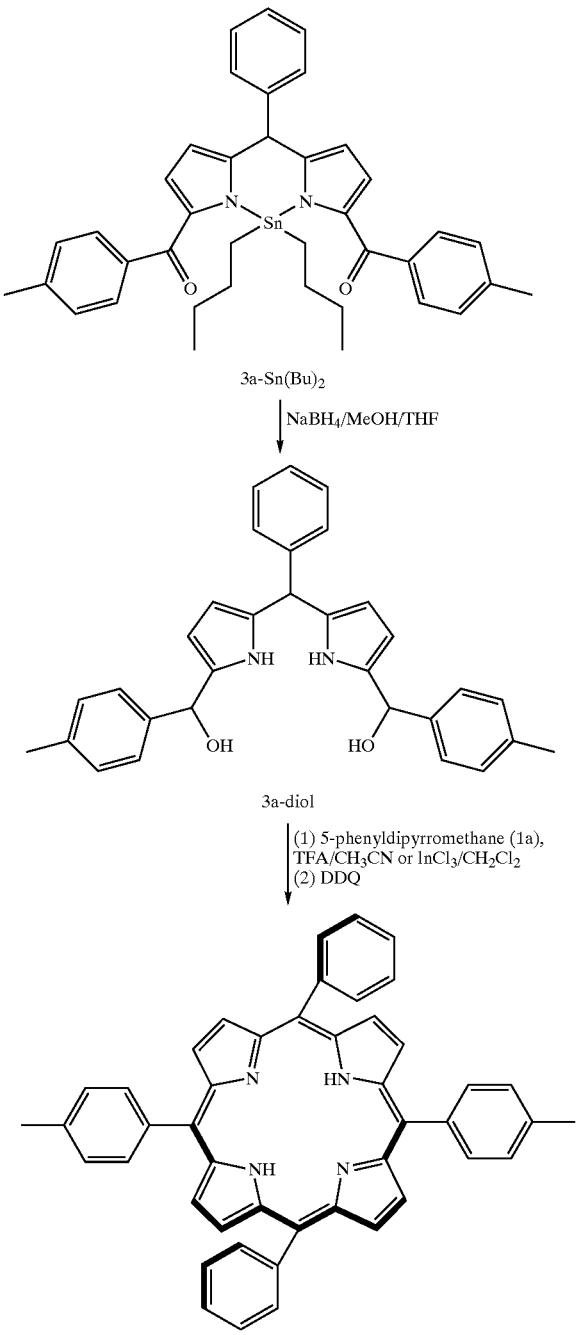

The foregoing is illustrative of the present invention, and is not to be construed as limiting thereof. The invention is defined by the following claims, with equivalents of the claims to be included therein.

What is claimed is:

1. A method of making a metal complex, comprising the steps of:
   (a) acylating a dipyrromethane or a 1-monoacyldipyrromethane to form a mixed reaction product comprising a 1,9-diacyldipyrromethane;
   (b) combining said mixed reaction product with a compound of the formula $R_2MX_2$ in the presence of a base, where R is alkyl or aryl, M is Sn, Si, Ge, or Pb, and X is halo, OAc, acac or OTf, to form a metal complex of the formula $DMR_2$ in said mixed reaction product, wherein D is a 1,9-diacyldipyrromethane; and then
   (c) separating said metal complex from said mixed reaction product.

2. The method of claim 1, wherein said acylating step (a) is carried out by reacting said dipyrromethane or 1-monoacyldipyrromethane with a compound of the formula $R^3COX$, where $R^3$ is alkyl or aryl and X is halo, to form said mixed reaction product comprising a 1,9-diacyldipyrromethane acylated at the 1 and 9 positions with $R^3CO—$.

3. The method of claim 1, wherein said acylating step (a) is carried out by reacting said dipyrromethane or 1-monoacyldipyrromethane with an acid chloride and a Grignard reagent to form said mixed reaction product comprising a 1,9-diacyldipyrromethane.

4. The method of claim 1, wherein said acylating step (a) is carried out by reacting said dipyrromethane or 1-monoacyldipyrromethane with an active ester to form said mixed reaction product comprising a 1,9-diacyldipyrromethane.

5. The method of claim 1, wherein said acylating step (a) is carried out by reacting said dipyrromethane or 1-monoacyldipyrromethane with a Vilsmeier reagent to form said mixed reaction product comprising a 1,9-diacyldipyrromethane.

6. The method of claim 1, wherein said base is selected from the group consisting of triethylamine, tributylamine, N,N-diisopropylamine, DBU, DBN, and 2,6,-di-tert-butylpyridine.

7. The method of claim 1, wherein M is Sn.

8. The method of claim 1, wherein said acylating step (a) is carried out with a dipyrromethane which is thereby acylated at the 1 and 9 position to produce said 1,9-diacyldipyrromethane.

9. The method of claim 1, wherein said acylating step (a) is carried out with a 1-monoacyldipyrromethane which is acylated at the 9 position to produce said 1,9-diacyldipyrromethane.

10. The method of claim 1, wherein said compound of the formula $R_2MX_2$ is immobilized on a solid support.

11. The method of claim 1, further comprising the step of:
    (d) treating said metal complex with an acid to produce a 1,9-diacyldipyrromethane.

12. The method of claim 11, wherein said acid is selected from the group consisting of trifluoroacetic acid, trichloroacetic acid, acetic acid, HCl, p-toluene sulfonic acid.

13. The method of claim 1, further comprising the steps of:
    (d) reducing said metal complex with a reducing agent to form a diol from said 1,9-diacyldipyrromethane; and then
    (e) condensing said diol with a dipyrromethane to form a porphyrin ring compound therefrom.

14. The method of claim 13, wherein said reducing agent is $NaBH_4$.

15. The method of claim 1, wherein said dipyrromethane is substituted at the 5 position with a substituent selected from the group consisting of H, alkyl, and aryl.

16. The method of claim 1, wherein said dipyrromethane is substituted at the 5 position with a substituent selected from the group consisting of dipyrromethane, porphyrin, dipyrrin, and diacyldipyrromethane.

17. A method of making a metal complex, comprising:
    reacting a 1,9-diacyldipyrromethane with a compound of the formula $R_2MX_2$ in the presence of a base, where R is alkyl or aryl, M is Sn, Si, Ge or Pb, and X is halo, OAc, acac or OTf, to form a metal complex of the general formula $DMR_2$, wherein D is said 1,9-diacyldipyrromethane.

18. The method of claim 17, wherein said base is selected from the group consisting of triethylamine, tributylamine, N,N-diisopropylamine, DBU, DBN, and 2,6,-di-tert-butylpyridine.

19. The method of claim 17, wherein M is Sn.

20. A metal complex of the general formula $DMR_2$, wherein D is a 1,9-diacyldipyrromethane, M is Sn, Si, Ge, or Pb, and R is alkyl or aryl.

21. The metal complex of claim 20, wherein M is Sn.

22. The metal complex of claim 20, wherein said dipyrromethane is substituted at the 5 position with a substituent selected from the group consisting of H, alkyl, and aryl.

23. The metal complex of claim 20, wherein said dipyrromethane is substituted at the 5 position with a substituent selected from the group consisting of dipyrromethane, porphyrin, dipyrrin, and diacyldipyrromethane.

* * * * *

UNITED STATES PATENT AND TRADEMARK OFFICE
CERTIFICATE OF CORRECTION

PATENT NO. : 6,924,375 B2
APPLICATION NO. : 10/654181
DATED : August 2, 2005
INVENTOR(S) : Lindsey et al.

It is certified that error appears in the above-identified patent and that said Letters Patent is hereby corrected as shown below:

On the Title Page,
Item (56) should include the following:
Under U.S. PATENT DOCUMENTS
6,420,648    7/2002
6,559,374    5/2003
6,603,070    8/2003
6,642,376    11/2003
20030096978    5/2003
10/641,412    8/2003

On Title Page Item (56)
Under OTHER PUBLICATIONS
Gryko et al.; "Parallel synthesis of *meso*-substituted corroles and *meso*-substituted [22]pentaphyrins(1.1.1.0.0) from diacyldipyrromethanes" *J. Porphyrins Phtalocyanines* 7 239-248 (2003).

Rao et al.; "Rational Syntheses of Porphyrins Bearing up to Four Different Meso Substituents" *J. Org. Chem.* 2000 65, 7323-7344 (2000).

UNITED STATES PATENT AND TRADEMARK OFFICE
CERTIFICATE OF CORRECTION

PATENT NO. : 6,924,375 B2 Page 2 of 2
APPLICATION NO. : 10/654181
DATED : August 2, 2005
INVENTOR(S) : Lindsey et al.

It is certified that error appears in the above-identified patent and that said Letters Patent is hereby corrected as shown below:

Columns 32 and 34
The first line of Scheme 8 should read

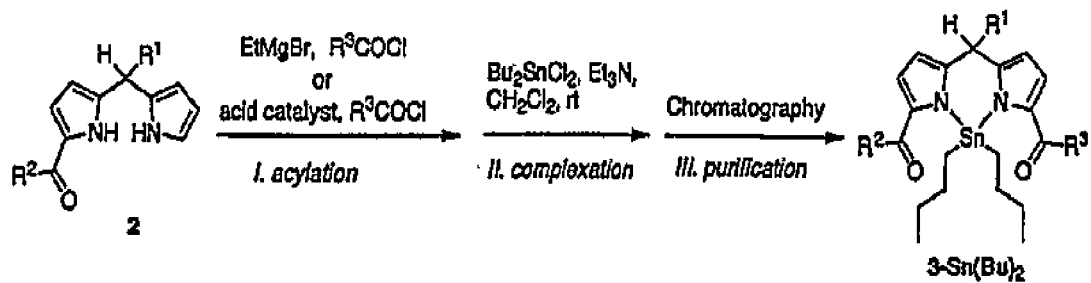

Signed and Sealed this

Twenty-sixth Day of December, 2006

JON W. DUDAS
*Director of the United States Patent and Trademark Office*